(12) United States Patent
Niazi et al.

(10) Patent No.: US 12,580,056 B2
(45) Date of Patent: Mar. 17, 2026

(54) PRODUCTION AND DELIVERY TRACKING AND SAMPLE VERIFICATION OF PATIENT-SPECIFIC THERAPEUTICS

(71) Applicant: NantCell, Inc., Culver City, CA (US)

(72) Inventors: Kayvan Niazi, Agoura Hills, CA (US); Nicholas James Witchey, Laguna Hills, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

(21) Appl. No.: 18/820,440

(22) Filed: Aug. 30, 2024

(65) Prior Publication Data

US 2024/0420811 A1    Dec. 19, 2024

Related U.S. Application Data

(60) Division of application No. 18/523,564, filed on Nov. 29, 2023, now Pat. No. 12,112,838, which is a
(Continued)

(51) Int. Cl.
*G16H 10/40*        (2018.01)
*G01N 33/58*        (2006.01)
(Continued)

(52) U.S. Cl.
CPC ............. *G16H 10/40* (2018.01); *G01N 33/58* (2013.01); *G06F 16/2379* (2019.01);
(Continued)

(58) Field of Classification Search
None
See application file for complete search history.

(56) References Cited

U.S. PATENT DOCUMENTS 6,153,389 A    11/2000 Haarer et al.
8,676,509 B2    3/2014 De La Torre-Bueno
(Continued)

FOREIGN PATENT DOCUMENTS

WO    WO-2005093641 A1 * 10/2005 .............. B01L 3/545

OTHER PUBLICATIONS

Koczula et al., "Lateral flow assays," Essays in Biochemistry, 60: 111-120 (2016).
(Continued)

*Primary Examiner* — Devin C Hein
(74) *Attorney, Agent, or Firm* — Harness Dickey & Pierce P.L.C.

(57)        ABSTRACT

Systems and methods for tracking biological samples are presented. Intrinsic and extrinsic biological sample data and/or intrinsic and extrinsic patient data may be used to label a biological sample obtained at a point-of-care facility, which may be sent to a processing facility, wherein the labeled biological sample undergoes analysis and/or processing into a labeled therapeutic. The labeled therapeutic is delivered back to the point-of-care facility, wherein the labeled therapeutic is tested for the presence of the additives prior to administration to a patient. Multi-factor validation is performed, including validating the identity of the patient to a container, validating the identity of the labeled biological sample/therapeutic to the container, and thus, validating the identity of the labeled therapeutic to the patient. The entire life cycle of a biological sample used to generate a personalized therapeutic is validated, and ensures that mix-ups or errors in administration are reduced or eliminated.

20 Claims, 8 Drawing Sheets

Related U.S. Application Data continuation of application No. 16/561,773, filed on Sep. 5, 2019, now Pat. No. 11,894,109.

(60) Provisional application No. 62/745,746, filed on Oct. 15, 2018.

(51) Int. Cl.
    G06F 16/23     (2019.01)
    G06Q 50/04     (2012.01)
    G16H 20/10     (2018.01)

(52) U.S. Cl.
    CPC ............. G06Q 50/04 (2013.01); G16H 20/10 (2018.01); G06Q 2220/00 (2013.01)

(56) References Cited

U.S. PATENT DOCUMENTS

| | | | |
|---|---|---|---|
| 9,262,719 | B2 | 2/2016 | Soon-Shiong |
| 2004/0048259 | A1 | 3/2004 | Hashmi et al. |
| 2007/0008523 | A1 | 1/2007 | Kaye et al. |
| 2007/0122824 | A1 | 5/2007 | Tucker et al. |
| 2008/0019924 | A1 | 1/2008 | Kittler et al. |
| 2008/0235055 | A1 | 9/2008 | Mattingly et al. |
| 2009/0084981 | A1 | 4/2009 | Bown et al. |
| 2011/0015945 | A1 | 1/2011 | Addy |
| 2012/0041778 | A1 | 2/2012 | Kraft |
| 2015/0039342 | A1 | 2/2015 | Chen et al. |
| 2015/0332283 | A1 | 11/2015 | Witchey |
| 2017/0193167 | A1* | 7/2017 | Wood ..................... G16H 20/40 |
| 2018/0096175 | A1 | 4/2018 | Schmeling et al. |
| 2024/0096458 | A1 | 3/2024 | Niazi et al. |

OTHER PUBLICATIONS

Gwyn et al., "Lateral flow-based antibody testing for Chlamydia trachomatis," Journal of Immunological Methods, 435: 27-31 (2016).
Grimms. J., "New Fluorescent Dyes Could Advance Biological Imaging," HHMI, pp. 1-7 (2017).
Grimms, J., "A general method to fine-tune fluorophores for live-cell and in vivo imaging," Nature Methods (2017).
Office Action from corresponding U.S. Appl. No. 16/561,773, dated Sep. 13, 2022.
Final Office Action from corresponding U.S. Appl. No. 16/561,773, dated Jan. 20, 2023.
Advisory Action from corresponding U.S. Appl. No. 16/561,773, dated Apr. 6, 2023.
Office Action from corresponding U.S. Appl. No. 16/561,773, dated Jun. 13, 2023.
Haser, How Later Flow Assays Work, Dec. 2, 2017, pp. 1-9, https://nanohybrids.net/blogs/nanoparticles/how-lateral-flow-assays-work (Year: 2019).
Levine et al., Global Manufacturing of CAR T Cell Therapy, Dec. 31, 2016, Molecular Therapy Methods & Clinical Development, vol. 4, 17, pp. 92-101, https://doi.org/10.1016/j.omtm.2016.12.006 (Year: 2016).
Kario Perica, et al., Building a CAR Garage: Preparing for the Delivery of Commercial CAR T Cell Products at Memorial Sloan Kettering Cancer Center, Biology of Blood and Marrow Transplantation, vol. 24, Issue 6, 2018, pp. 1135-1141, ISSN 1083-8791, https://doi.org/10.1016/j.bbmt.2018.02.018. (Year: 2018).
Hartmann J, Schüßler-Lenz M, Bondanza A, Buchholz CJ. Clinical development of CAR T cells-challenges and opportunities in V translating innovative treatment concepts. EMBO Mol Med. Sep. 2017;9(9):1183-1197. doi: 10.15252/emmm.201607485. PMID: 28765140; PMCID: PMC5582407. (Year: 2017).
Kaiser, A., Assenmacher, M., Schröder, B. et al. Towards a commercial process for the manufacture of genetically modified T cells for therapy. Cancer Gene Ther22, 72-78 (2015). https://doi.org/10.1038/cgt.2014.78 (Year: 2015).
Sylim et al., Blockchain Technology for Detecting Falsified and Substandard Drugs in Distribution: Pharmaceutical Supply Chain Intevention, Sep. 13, 2018, JMIR Res Protoc 2018; 7(9):e10163 (Year: 2018).
Notice of Allowance from corresponding U.S. Appl. No. 16/561,773, dated Sep. 28, 2023.
Notice of Allowance from corresponding U.S. Appl. No. 18/523,564 dated Jul. 3, 2024.
Lamb M, Margolin RE, Vitale J. (2018). Personalized supply chains for cell therapies. Cell Gene Therapy Insights, 3:815-833.

\* cited by examiner

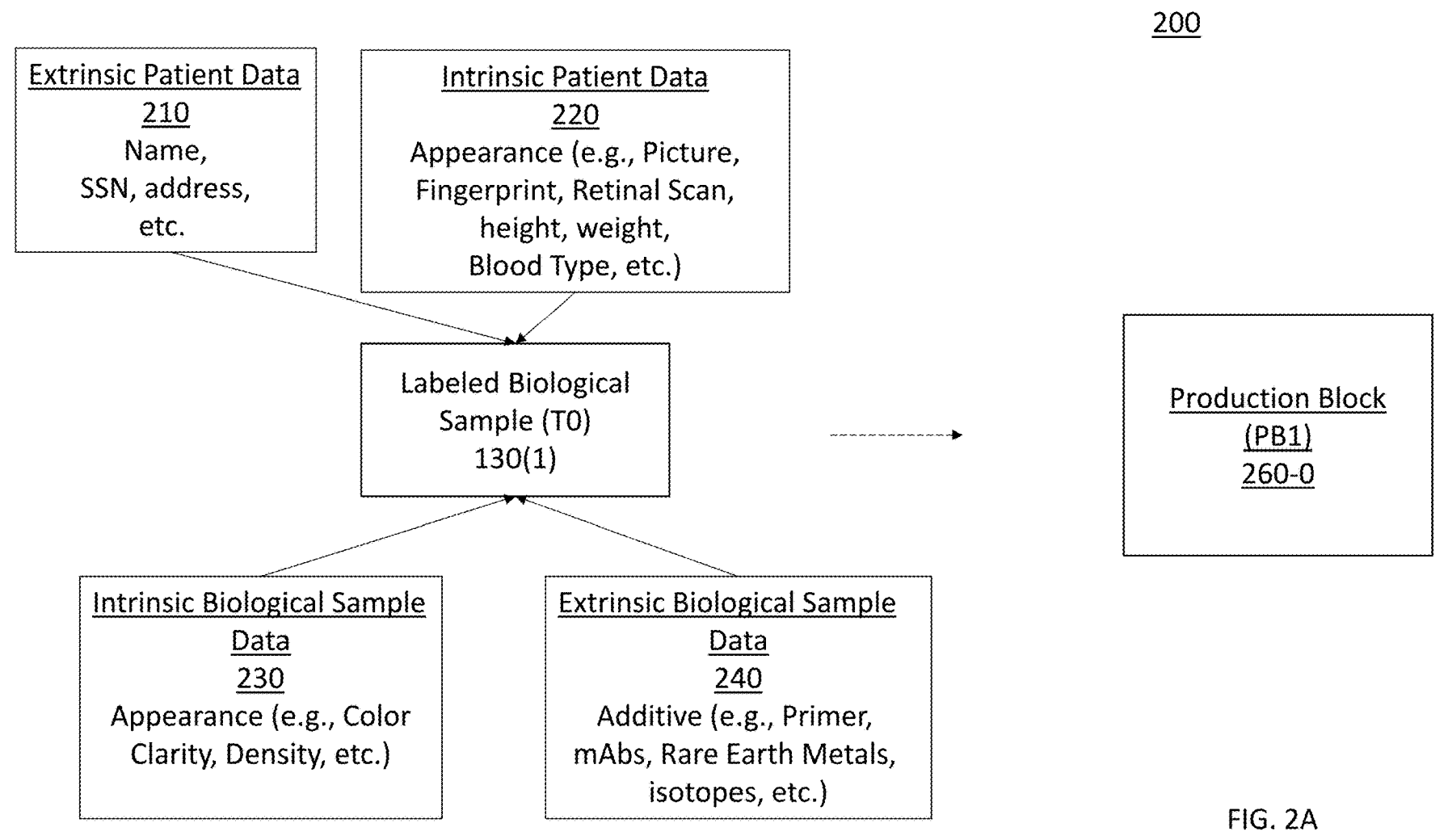

200

Extrinsic Patient Data
210
Name,
SSN, address,
etc.

Intrinsic Patient Data
220
Appearance (e.g., Picture,
Fingerprint, Retinal Scan,
height, weight,
Blood Type, etc.)

Labeled Biological
Sample (T0)
130(1)

Extrinsic Biological Sample
Data
240
Additive (e.g., Primer,
mAbs, Rare Earth Metals,
isotopes, etc.)

Intrinsic Biological Sample
Data
230
Appearance (e.g., Color
Clarity, Density, etc.)

Production Block
(PB1)
260-0

FIG. 2A

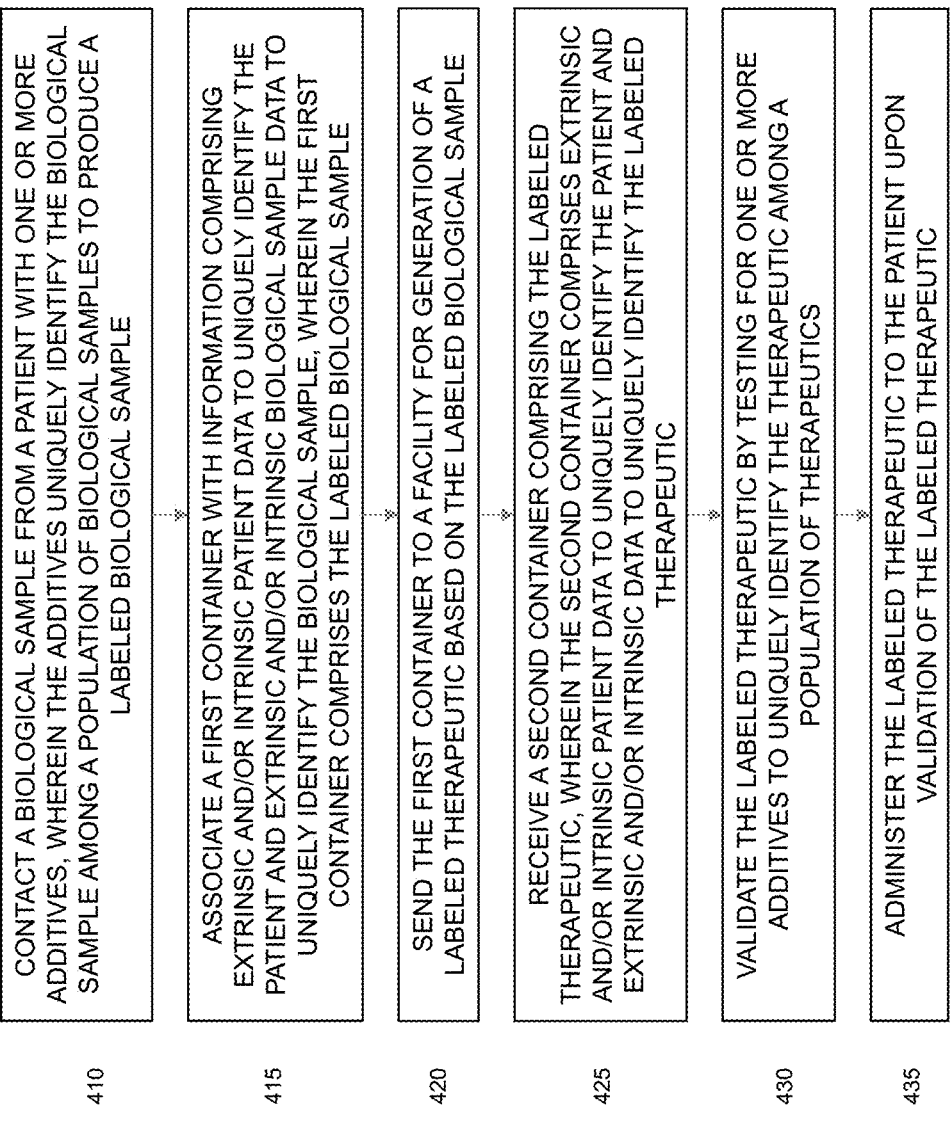

CONTACT A BIOLOGICAL SAMPLE FROM A PATIENT WITH ONE OR MORE ADDITIVES, WHEREIN THE ADDITIVES UNIQUELY IDENTIFY THE BIOLOGICAL SAMPLE AMONG A POPULATION OF BIOLOGICAL SAMPLES TO PRODUCE A LABELED BIOLOGICAL SAMPLE

410

ASSOCIATE A FIRST CONTAINER WITH INFORMATION COMPRISING EXTRINSIC AND/OR INTRINSIC PATIENT DATA TO UNIQUELY IDENTIFY THE PATIENT AND EXTRINSIC AND/OR INTRINSIC BIOLOGICAL SAMPLE DATA TO UNIQUELY IDENTIFY THE BIOLOGICAL SAMPLE, WHEREIN THE FIRST CONTAINER COMPRISES THE LABELED BIOLOGICAL SAMPLE

415

SEND THE FIRST CONTAINER TO A FACILITY FOR GENERATION OF A LABELED THERAPEUTIC BASED ON THE LABELED BIOLOGICAL SAMPLE

420

RECEIVE A SECOND CONTAINER COMPRISING THE LABELED THERAPEUTIC, WHEREIN THE SECOND CONTAINER COMPRISES EXTRINSIC AND/OR INTRINSIC PATIENT DATA TO UNIQUELY IDENTIFY THE PATIENT AND EXTRINSIC AND/OR INTRINSIC DATA TO UNIQUELY IDENTIFY THE LABELED THERAPEUTIC

425

VALIDATE THE LABELED THERAPEUTIC BY TESTING FOR ONE OR MORE ADDITIVES TO UNIQUELY IDENTIFY THE THERAPEUTIC AMONG A POPULATION OF THERAPEUTICS

430

ADMINISTER THE LABELED THERAPEUTIC TO THE PATIENT UPON VALIDATION OF THE LABELED THERAPEUTIC

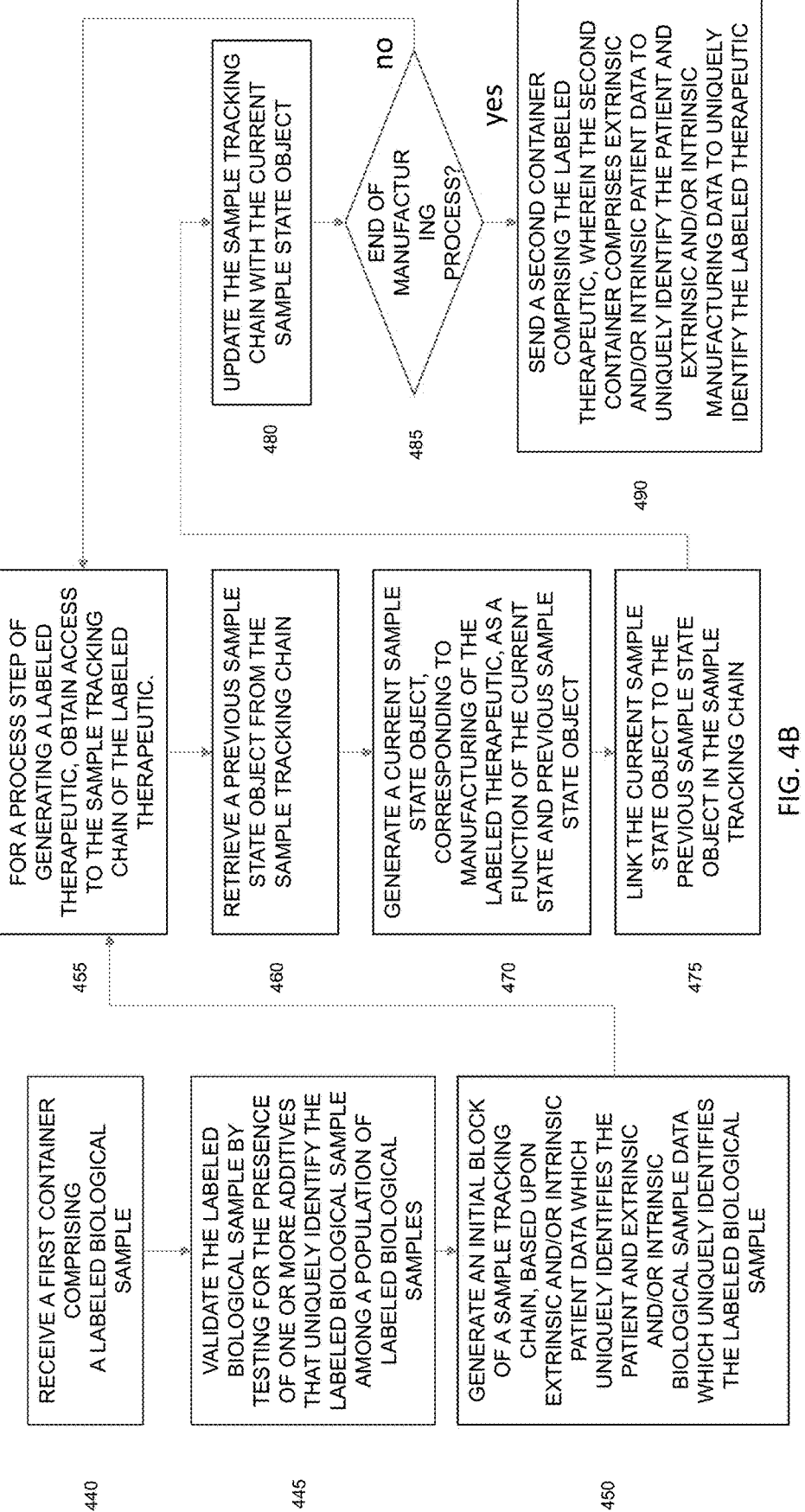

FOR A PROCESS STEP OF GENERATING A LABELED THERAPEUTIC, OBTAIN ACCESS TO THE SAMPLE TRACKING CHAIN OF THE LABELED THERAPEUTIC. — 455

RETRIEVE A PREVIOUS SAMPLE STATE OBJECT FROM THE SAMPLE TRACKING CHAIN — 460

GENERATE A CURRENT SAMPLE STATE OBJECT, CORRESPONDING TO MANUFACTURING OF THE LABELED THERAPEUTIC, AS A FUNCTION OF THE CURRENT STATE AND PREVIOUS SAMPLE STATE OBJECT — 470

LINK THE CURRENT SAMPLE STATE OBJECT TO THE PREVIOUS SAMPLE STATE OBJECT IN THE SAMPLE TRACKING CHAIN — 475

UPDATE THE SAMPLE TRACKING CHAIN WITH THE CURRENT SAMPLE STATE OBJECT — 480

END OF MANUFACTURING PROCESS? — 485 no yes

SEND A SECOND CONTAINER COMPRISING THE LABELED THERAPEUTIC, WHEREIN THE SECOND CONTAINER COMPRISES EXTRINSIC AND/OR INTRINSIC PATIENT DATA TO UNIQUELY IDENTIFY THE PATIENT AND EXTRINSIC AND/OR INTRINSIC MANUFACTURING DATA TO UNIQUELY IDENTIFY THE LABELED THERAPEUTIC — 490

RECEIVE A FIRST CONTAINER COMPRISING A LABELED BIOLOGICAL SAMPLE — 440

VALIDATE THE LABELED BIOLOGICAL SAMPLE BY TESTING FOR THE PRESENCE OF ONE OR MORE ADDITIVES THAT UNIQUELY IDENTIFY THE LABELED BIOLOGICAL SAMPLE AMONG A POPULATION OF LABELED BIOLOGICAL SAMPLES — 445

GENERATE AN INITIAL BLOCK OF A SAMPLE TRACKING CHAIN, BASED UPON EXTRINSIC AND/OR INTRINSIC PATIENT DATA WHICH UNIQUELY IDENTIFIES THE PATIENT AND EXTRINSIC AND/OR INTRINSIC BIOLOGICAL SAMPLE DATA WHICH UNIQUELY IDENTIFIES THE LABELED BIOLOGICAL SAMPLE — 450

FIG. 4B

PRODUCTION AND DELIVERY TRACKING AND SAMPLE VERIFICATION OF PATIENT-SPECIFIC THERAPEUTICS

CROSS-REFERENCE TO RELATED APPLICATIONS

This application is a divisional of U.S. patent application Ser. No. 18/523,564, filed on 29 Nov. 2023, which is a continuation of U.S. patent application Ser. No. 16/561,773, filed on 5 Sep. 2019. This application claims the benefit of U.S. Provisional Patent Application No. 62/745,746, filed on 15 Oct. 2018. The entire disclosures of each of the above applications are incorporated herein by reference.

FIELD OF THE INVENTION

The field of the invention is digital tracking and sample verification technologies, and in particular, digital tracking and sample verification technologies for production and delivery of patient-specific therapeutics such as viral vaccines.

BACKGROUND

The background description includes information that may be useful in understanding the systems and methods described herein. It is not an admission that any of the information provided herein is prior art, or that any publication specifically or implicitly referenced is prior art.

The advent of personalized medicine has allowed patient-specific therapeutics to be developed that are specifically tailored to treat individual patients. For example, biological material may be obtained from a patient, provided to a manufacturer of a patient-specific therapeutic, and delivered to the patient for administration. For example, a patient-specific cancer therapeutic such as CAR T-cells may be engineered to express a chimeric antigen receptor, wherein the starting materials comprise immune cells (e.g., T-cells) obtained from a patient. The engineered CAR T-cells may be administered to the patient from which the biological material was obtained. In other cases, a neoepitope or neoantigen may be determined from analysis of the tumor cell, and an antibody-based therapeutic may be generated based on this information. In still other cases, viral or yeast-based vaccines may be designed and manufactured for administration to a patient to treat or prevent a particular type of cancer or other viral-related disease.

As personalized medicine is specifically tailored to an individual, it is important to ensure that mix-ups do not occur during any part of this process, beginning with obtaining a biological sample from an individual, through manufacturing a personalized therapeutic, and ending with delivery and administration of the therapeutic to the patient at a point of care. Delivery of a therapeutic to a patient other than to whom the therapy is tailored to may have adverse side effects (e.g., triggering an anaphylactic response), may fail to effectively treat the disease, and may potentially expose the patient to other diseases (e.g., diseases present in the patient from which the biological material was obtained).

Typically, biological samples are extrinsically labeled. For example, a biological sample may be labeled with extrinsic information (e.g., a patient's name, a bar code, etc.) affixed to its container. However, biological samples being processed through a workflow (e.g., by a technician, etc.) may be mislabeled and/or mixed up during manufacturing and processing. This may result in improper manufacturing of the patient-specific therapeutic (e.g., if workflows are switched, etc.) and/or may result in administration of the wrong therapeutic to a patient.

Examples of biological tracking systems are provided in the art. For example, U.S. Pat. No. 8,676,509 to De La Torre-Beuno entitled "System for Tracking Biological Samples", filed Nov. 13, 2002, provides real-time tracking of samples from collection through storage. Samples are associated with unique bar code identifiers that link to processing steps at various workstations. Such an approach aids in reducing possible processing errors with respect to managing tissue slides. However, the system still requires significant manual processing to tag the samples, and therefore, mix-ups are still possible.

As another example, U.S. Patent Application Publication No. US 2008/0235055 to Mattingly et al. entitled "Laboratory Instrumentation Information Management and Control Network", filed Jun. 13, 2007, discusses forming a harmonized specimen identifier from a case identifier of a patient and a specimen identifier. The harmonized specimen identifier represents a combination of identifiers arranged in a defined format, where the various identifiers aid in tracking a specimen at different points in a workflow.

More recently, blockchain technology has been proposed for use with supply chain tracking. Various blockchain technologies are available including Microsoft's Confidential Consortium (CoCo), enterprise-level blockchain approaches such as openchain (www.openchain.org) and Ethereum, and Intel's Sawtooth Lake (https://intelledger-.github.io/0.7/introduction.html), a distributed ledger platform that implements data models and transaction language using one or more transaction families.

However, all of these approaches are geared towards tracking the container in which the biological sample is placed and mix-ups are still possible. Thus, there remains a considerable need for improved tracking and verification systems to reduce or eliminate sample mix-ups during processing and administration of personalized therapeutics.

SUMMARY

The subject matter described herein provides systems, computer readable media, and methods in which biological samples may be electronically tracked and/or verified throughout their entire lifecycle using a combination of intrinsic and extrinsic patient data and intrinsic and extrinsic biological sample data. In some aspects, the intrinsic and extrinsic data may be coupled with a sample tracking chain (e.g., a digital chain of sample states, a blockchain, digital ledger, etc.) to track the biological sample through an analysis and/or manufacturing workflow to produce the personalized therapeutic.

In an aspect of the subject matter described herein, methods, systems, and computer readable media are provided for linking extrinsic and intrinsic data of the patient and/or biological sample. This approach allows the biological sample and/or therapeutic, the container in which the biological sample and/or therapeutic is placed, and the patient to which the therapeutic is to be administered to be linked.

In another aspect of the subject matter described herein, methods, systems, and computer readable media are provided for a biological sample tracking system that includes one or more sample databases, one or more sample tracking engines, and may also include one or more sample search engines. The sample database may include a computing device configured to store sample tracking chains (i.e., a chain of biological sample states throughout an analysis and manufacturing life cycle of the biological sample) on a non-transitory, computer-readable memory. The sample tracking chain may include a linked chain of digital state objects, wherein each state object is instantiated to represent the biological sample at a particular point in an analysis and/or therapeutic manufacturing workflow. In some cases, additives may be added at various stages during processing to identify the biological sample and/or therapeutic.

The sample tracking engine may be implemented using a computing device (e.g., a server, a workstation, a cell phone, a cloud device, a distributed computing system, etc.) coupled with the sample database via a computer network or an internal communication bus. The sample tracking engine comprises at least one processor and computer readable, non-transitory memory storing software instructions. Upon execution of the software instructions by the processor, the sample tracking engine is configurable to process one or more states of a biological sample. The sample tracking engine obtains access to at least one sample tracking chain in the sample database wherein the sample tracking chain relates to the biological sample and retrieves at least one previous sample state object comprising a block of data from a previous sample state. The sample tracking engine generates a current sample state object or representation based on the previous sample state object and the current state. The current state may include intrinsic and/or extrinsic manufacturing data of the biological sample. Using the previous sample state object and the current state, the sample tracking engine instantiates or otherwise derives a current sample state object and links the current sample state object to the previous sample state object in the sample tracking chain. In some embodiments, the sample tracking chain comprises a blockchain. The sample tracking engine also may update the sample tracking chain in the sample database so that the sample tracking chain includes the current sample state object.

According to aspects of the methods, systems, and computer readable media provided herein, a biological sample obtained from a patient is tracked using one or more of extrinsic and intrinsic patient data, intrinsic and extrinsic biological sample data, and extrinsic and intrinsic analysis and/or manufacturing data. The use of multiple types of data allows multi-factor authentication, including three-factor authentication or higher, thereby allowing the biological sample, the container in which the biological sample is placed, as well as the identity of the patient to be linked, in order to ensure that the correct therapeutic is administered to the patient. In some aspects, the therapeutic may be assayed prior to administration to the patient at a point of care facility, and the results of the assay may be compared to intrinsic and/or extrinsic patient data and/or intrinsic and/or extrinsic biological sample data.

Various objects, features, aspects and advantages of the subject matter described herein will become more apparent from the following detailed description of preferred embodiments, along with the accompanying drawing figures in which like numerals represent like components.

BRIEF DESCRIPTION OF THE DRAWINGS

FIGS. 2A-2C show example schematics of tracking a biological sample using extrinsic and intrinsic patient data, extrinsic and intrinsic biological sample data, and extrinsic and intrinsic manufacturing data throughout the biological sample life cycle, according to embodiments of the techniques disclosed herein.

FIGS. 4A-4B represent an example operational flowchart of tracking biological samples via intrinsic and extrinsic data using sample tracking chains, according to embodiments of the techniques disclosed herein.

DETAILED DESCRIPTION

Figure 1:
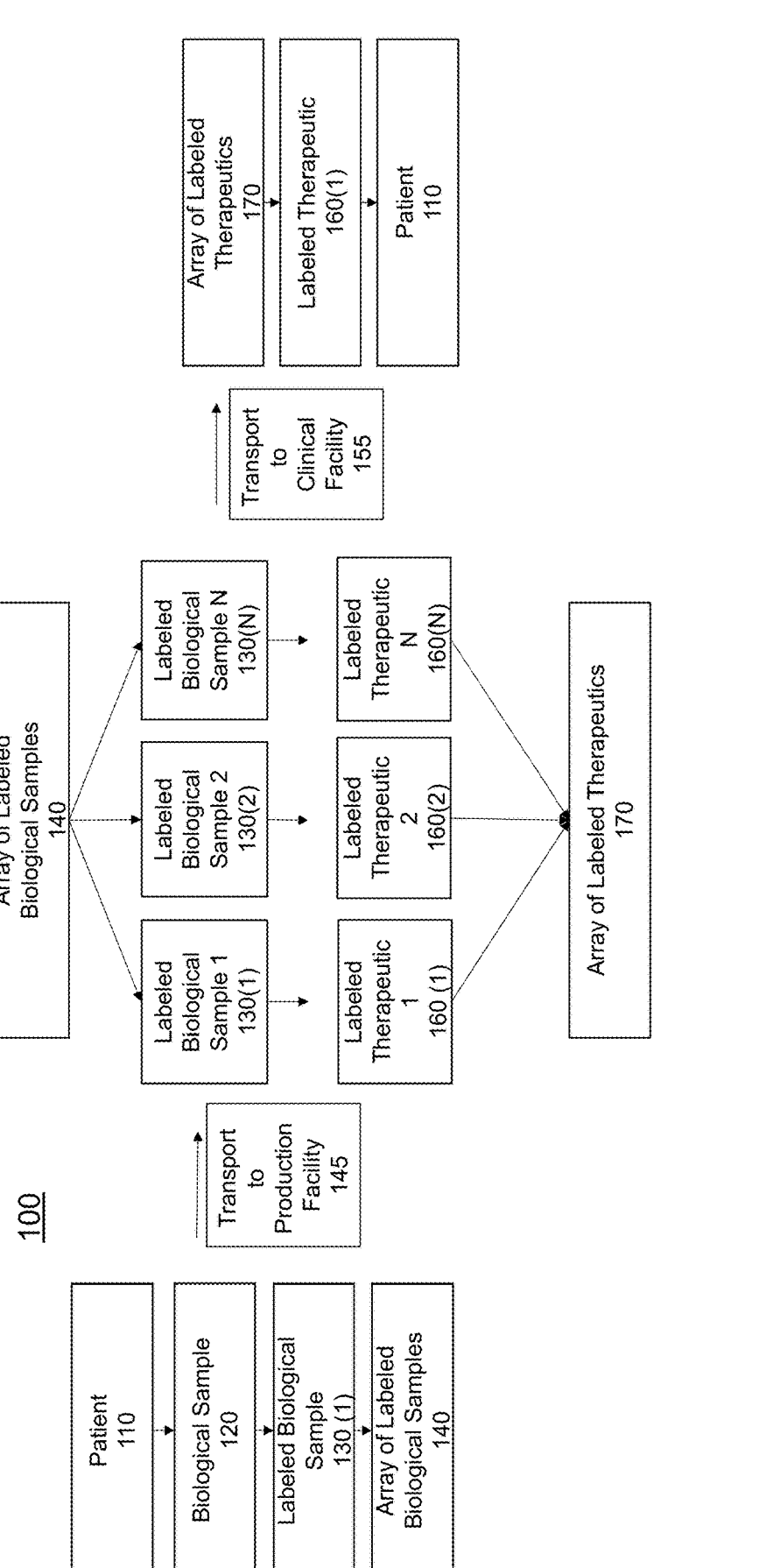
FIG. 1 is an overview of a patient-specific biological sample life cycle, according to an embodiment of the techniques disclosed herein.

In general, any language directed to a computer should be read to include any suitable combination of computing devices, including servers, interfaces, systems, tablets, mobile devices, distributed systems, databases, agents, peers, engines, controllers, modules, or other types of computing devices operating individually or collectively. One of skill in the art will appreciate that the computing devices comprise at least one processor configured to execute a computer program product comprising software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed system. Further, the disclosed technologies can be embodied as a computer program product that includes a non-transitory computer readable medium storing the software instructions that cause a processor to execute the disclosed steps associated with implementations of computer-based algorithms, processes, methods, or other instructions. In some embodiments, the various servers, systems, databases, or interfaces may exchange data using standardized protocols or algorithms, possibly based on HTTP, HTTPS, TCP/IP, UPD/IP, AES, public-private key exchanges, web service APIs, known transaction protocols, or other electronic information exchanging methods. Data exchanges among devices can be conducted over a packet-switched network, the Internet, LAN, WAN, VPN, or other type of packet switched network, a circuit switched network, cell switched network, or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on data or data objects stored in the memory.

In some embodiments, the biological sample may be converted into a therapeutic. In other embodiments, the biological sample may be used to derive a therapeutic or otherwise produce a therapeutic; a patient specific composition of matter for example. Thus, a life cycle of the biological sample may include obtaining the biological sample, producing the therapeutic based upon the biological sample, and administering the therapeutic to the patient.

One of skill in the art will appreciate that the disclosed techniques provide many advantageous technical effects including validation of the contents of a biological sample or therapeutic relative to a specific patient and to the container in which the biological sample or therapeutic is placed. In some aspects, the manufacturing process of the biological sample into the therapeutic may also be tracked using a sample tracking chain. Accordingly, the present techniques greatly improve the validity and fidelity of personalized therapeutics or biologics, helping to ensure that a particular personalized therapeutic is manufactured to have a specific effect and is administered to a specific patient. Still other advantages of the techniques presented herein include the ability to backtrack through the sample tracking chain to previous states (e.g., from T3 to T2, from T2 to T1, from T1 to T0), in order to reconstruct features of a biological sample/therapeutic at a previous state. Through the use of a sample tracking chain data structure stored in memory, intrinsic information about a biological sample can be used as an index to access biological sample information, and in some cases, without needing additional extrinsic information.

Present techniques enable construction or configuration of a computing device to operate on vast quantities of digital data in the form of processing and manufacturing biological samples/therapeutics, with precision and accuracy exceeding human capabilities. The digital data of the sample tracking chain represents biological/therapeutic samples or sample states, and is not the sample itself.

The following discussion provides many example embodiments of the subject matter described herein. Although each embodiment represents a single combination of elements, the subject matter described herein is considered to include all possible combinations of the disclosed elements. Thus if one embodiment comprises elements A, B, and C, and a second embodiment comprises elements B and D, then the subject matter described herein is also considered to include other remaining combinations of A, B, C, or D, even if not explicitly disclosed. Further, the term of the form "at least one of A, B, and C" should be interpreted as any combination of elements alone or in combination unless otherwise excepted.

As used herein, and unless the context dictates otherwise, the term "coupled to" is intended to include both direct coupling (in which two elements that are informationally coupled to each other contact each other) and indirect coupling (in which at least one additional element is located between the two elements). Therefore, the terms "coupled to" and "coupled with" are used synonymously.

The following figures and description include the entire life cycle of a biological sample/therapeutic, from obtaining the biological sample from a patient, through production of the therapeutic, and administration of the therapeutic (e.g., derived from the biological sample and manufactured to have a certain activity based on analysis or modification of the biological sample, etc.) to a specific patient at a point of care.

Present techniques may also include tracking portions of the sample life cycle. For example, in some aspects, a personalized therapeutic may be manufactured based on analysis of the biological sample, and therefore, tracking of the biological sample may be limited to obtaining a sample from a patient and performing assays upon the biological sample. In this case, the therapeutic may be manufactured or selected based upon an analysis of the biological sample, and not derived directly from material of the biological sample. For example, a biological sample comprising cancer cells may be assayed to determine which chemotherapeutic(s) or biologic(s) (e.g., mAbs, etc.) that a patient's particular cancer is sensitive to. Once this information is available, the physician may select the appropriate treatment or combination of treatments for the patient. Therefore, tracking of the biological sample may begin upon obtaining the biological sample from the patient and may end upon analysis of the sample at a laboratory or other processing facility.

In other cases, the sample tracking techniques may be employed beginning at the site of therapeutic manufacturing through delivery and administration of the therapeutic to a patient. In still other cases, the biological sample may be tracked beginning with obtaining the sample from the patient, through analysis and manufacturing of the therapeutic, and continuing through delivery and administration to the patient. Accordingly, one of skill in the art will appreciate that there are many possible workflow variations in analysis of biological samples, manufacture and selection of corresponding therapeutics, and administration of the personalized therapeutic to a specific patient. Present techniques may be used for the entire life cycle of a biological sample, or for any portion or portions thereof.

In still other aspects, biological sample validation may be performed without tracking of manufacturing steps using a sample tracking chain. For example, the techniques described herein may be used for biological sample procurement and administration at the point of care (e.g., at the location at which the biological sample is obtained and the location at which the therapeutic is administered to the patient), and may involve limited tracking (e.g., input and output at a manufacturing facility, but not during actual manufacturing steps).

FIG. 1 shows an example sample workflow environment 100 in which the subject matter described herein is employed. Environment 100 is presented from the perspective of patient 110, wherein biological sample 120 is obtained from patient 110.

Biological sample 120 represents a biological sample obtained from patient 110. Biological samples include but are not limited to: blood, feces, hair, saliva, skin, tissue, urine, or other specimens obtained from patient 110. Any suitable technique may be used to obtain a biological sample from a patient. Although patient 110 is represented as a human, patient 110 may include any mammal or animal. Thus, the disclosed techniques are of value in other markets beyond human healthcare, and may apply in any situation where rigor is required to track samples or specimens over time.

Biological sample 120 is labeled to generate labeled biological sample 130(1) at the point of care. In some embodiments, the container in which the biological sample is placed may be labeled (e.g., with information pertaining to extrinsic and intrinsic patient data and/or intrinsic and extrinsic biological sample data). The biological sample itself may be labeled with one or more additives, which allows the biological sample to be linked to its container (e.g., linking the container or vial to the contents of the vial) and to the patient. Thus, the label may reflect both aspects of the biological sample (e.g., information pertaining to the number and type of additives) and aspects of the patient (e.g., information pertaining to the patient). Thus, the label may reflect aspects of the biological sample and the patient to link the container in which the biological sample is placed both to the patient and the biological sample itself.

It is contemplated that a point of care facility (e.g., a place where the biological sample is obtained and/or the therapeutic is administered) may obtain biological samples for a plurality of patients, for which personalized therapies are to be manufactured. Thus, in some aspects, vials of labeled biological samples will be placed into an array 140 for transport to a production/manufacturing or analysis facility, such that the contents of the vials are maintained separately. At the analysis and/or manufacturing facility, each biological sample may be subjected to analysis and/or a manufacturing protocol to produce a patient-specific therapeutic. Thus, it is important to ensure that biological samples are not mixed up, so that the correct therapeutic is administered to the correct patient. At operation 145, the array of biological samples 140 may be transported to production/analysis facility 145. It should be appreciated that at each step of a logistics chain, the sample can be verified and/or validated for tracking purposes.

Each sample of the array of biological samples 140 may be separated and subjected to a sample tracking protocol to produce a sample tracking chain (e.g., based on blockchain technology, distributed ledger technology, etc.). For example, labeled biological sample 130(1) may comprise a breast cancer sample that is analyzed to identify the amino acid sequence of a predicted first neoepitope. A first protein sequence corresponding to the predicted first neoepitope may be manufactured and used to generate a corresponding personalized first therapeutic 160(1) (e.g., a scFv or mAb) that binds to the first protein sequence.

As another example, labeled biological sample 130(2) may comprise liver cancer cells that are analyzed to identify an amino acid sequence of a predicted second neoepitope. A second protein sequence corresponding to the predicted second neoepitope may be manufactured and used to generate a corresponding personalized second therapeutic 160 (2) (e.g., a scFv or mAb that binds to the second protein sequence). As yet another example, labeled biological sample 130(N) may comprise T-cells from another patient, which are modified to produce CAR-T cells. Thus, each stage (or a subset of stages) of the manufacturing process for generating a personalized therapeutic for a specific patient may be tracked using a sample tracking process based on blockchain technology.

In general, the present techniques may be used to create patient specific therapies, including but not limited to, therapies that include and/or are derived from NK cells, T cells, dendritic cells, viruses, yeast, bacterial vaccines, etc. The labeled therapeutics 160(1)-160(N) may be combined in an array of therapeutics 170. At operation 155, the array of labeled therapeutics may be transported to a clinical or point of care facility. Each therapeutic is stored in a separate container during transport to the clinical facility.

Once arriving at the clinical facility, the array of labeled therapeutics 170 may be processed, such that each therapeutic is scheduled for administration to a specific patient. For example, labeled therapeutic 160(1) may be scheduled for administration to patient 110, from which the biological sample was obtained. Prior to administration to patient 110, the labeled therapeutic may be tested to ensure that the vial contains the proper therapeutic. Thus, the labeling on the vial may correspond both to the patient and to the therapeutic that it contains. Three validation steps may be performed to: link the patient to the therapeutic, link the patient to the vial, and link the vial to the therapeutic, wherein the validation steps may include at least one biological or chemical assay of the labeled therapeutic. In other cases, one or two of these validation steps may be performed. If validation of the labeled therapeutic prior to administration to the patient at the point of care fails, a notification is sent to a user (e.g., a doctor, medical personnel, a patient, etc.) regarding the failure. Similarly, if validation of the labeled biological sample fails at the manufacturing facility, a notification is sent to a user (e.g., a manufacturing technician, etc.) regarding the failure.

FIG. 2A shows various types of information that may be included to generate a labeled biological sample (T0). In some embodiments, the information associated with the labeled biological sample may be used to instantiate the initial block of a sample tracking chain for the biological sample, e.g., during production of a patient-specific therapeutic. In other embodiments, tracking technology may not be used during production of the therapeutic, but may still be used to track the biological sample from the point of care facility to the manufacturing facility and back again. These embodiments are described in additional detail as follows.

In some embodiments, the exterior of the vial may be labeled with extrinsic and/or intrinsic patient data in order to link the patient to the vial, and with extrinsic and/or intrinsic biological sample data to link the contents of the vial to the vial. In some embodiments, one or more additives may be added to the biological sample, and an assay may be performed on the biological sample to validate the contents of the vial.

Extrinsic patient data 210 may include identifying information specific to a patient or a combination of identifying information specific to a patient, including the name of the patient, a full or partial social security number of the patient, the age of the patient, the address of the patient, an image of the patient, a fingerprint, a biometric of the patient, or other extrinsic information (e.g., date at which the biological sample is obtained, location of collection, technician, physician, etc.) associated with the patient. This information may appear on the container into which the biological sample is placed. In some embodiments, this information may additionally be combined with any one or more of intrinsic patient data 220, intrinsic biological sample data 230, and extrinsic biological sample data 240, and may be provided to a hash function to generate a unique signature specific to the patient (e.g., as part of a sample tracking chain). The unique signature may be digitally associated with the container (e.g., linked through an identifier on the container such as a bar code, a Radio Frequency Identification (RFID) code, a Quick Response (QR) code, or a colorful QR code, etc.) or may be placed directly on the container itself. For example, biological sample 120 may be placed into a bio-safe container, to which an identifier is affixed.

Intrinsic patient data 220 may include various aspects of the physical appearance or other unique characteristics of the patient. For example, intrinsic patient data 220 may include a photograph of the patient, a finger print, an image from a retinal scan, a blood type, etc. This information may be used to independently verify the identity of the patient. In some aspects, intrinsic patient data 220 may be part of the label on the container into which the biological sample is placed. For example, a finger print of the patient may be placed on the container into which the biological sample is placed or perhaps an image of the patient's iris. The biological sample may be sent to the manufacturing facility and a patient-specific therapeutic may be generated. The therapeutic may then be sent to the point of care for administration to the patient, labeled with intrinsic patient data (e.g., the patient's fingerprint, facial recognition, retinal scan, etc.). In other embodiments, intrinsic patient data may include whole genome sequencing (WGS) data, which may be combined with phenotype information (e.g., hair color, eye color, etc.) to identify an individual. Prior to administration of the therapeutic, a fingerprint of the patient to which the therapeutic is to be administered may be obtained and compared to the fingerprint on the sample vial (e.g., a comparison may be performed visually or using imaging software to verify that the two sets of fingerprints are from the same patient). Using unique physical metrics from the patient provides a way to verify the identity of the patient. Such techniques may be useful for commonly occurring names (e.g., when multiple patients have the same or similar names, etc.). In general, the intrinsic patient data obtained at the time the biological sample is obtained may be compared to the intrinsic patient data obtained prior to administration of the therapeutic to validate that the therapeutic is being administered to the correct patient (e.g., by comparing fingerprints, retinal scans, iris, photographs, etc.).

In other embodiments, intrinsic patient data 220 may additionally be combined with extrinsic patient data 210, intrinsic biological sample data 230, and extrinsic biological sample data 240, and provided to a hash function to generate a unique signature specific to the patient (e.g., for creation of the initial block (T0) or genesis block). The unique signature may be digitally associated with the container or vial containing the biological sample, such as linked through an identifier on the vial (e.g., such as a bar code, a QR code, or a colorful QR code, etc.) or may be placed on the vial itself.

While extrinsic patient data provides a way to identify a patient, and intrinsic patient data may provide a way to further identify a patient and to verify that the extrinsic patient data is correctly associated with the vial, this information is limited to the relationship between the patient and the container, and does not link the contents of the container to the biological sample (from the patient) that resides in the container. Thus, intrinsic biological sample data 230 and/or extrinsic biological sample data 240 may be used for this purpose.

Intrinsic biological sample data 230 may include aspects of the appearance of the biological sample obtained from the patient. For example, appearance aspects may include color, clarity, density, size, shape, mass, weight, length, width, volume, tissue type, cell lines, genome or protein sequences (if analyzed by sequencing), location at which the sample was obtained, appearance of container in which the biological sample resides, or other metrics describing the biological sample. For example, if a blood sample is obtained from a patient, then the appearance characteristics will be commensurate with obtaining a blood sample.

Intrinsic biological sample data 230 may be encoded into the label of the biological sample 120. For example, biological sample data 230 may additionally be combined with extrinsic patient data 210, intrinsic patient data 220, and/or extrinsic biological sample data 240, and provided to a hash function to generate a unique signature specific to the patient (e.g., for creation of the initial block (T0) or genesis block). The unique signature may be digitally associated with the container or vial containing the biological sample, e.g., linked through an identifier on the vial (e.g., such as a bar code, a QR code, or a colorful QR code, etc.) or may be placed on the vial itself. Alternatively, intrinsic biological sample data 230 may be directly placed on the container.

Extrinsic biological sample data 240 may include unique additives or combinations thereof that are added to the biological sample. The biological sample may be later assayed to validate the integrity of the biological sample (e.g., by detecting the unique additive or combinations of additives present in within the biological sample). For example, unique additives or combinations thereof may include, but are not limited to, one or more primers, one or more monoclonal antibodies, one or more rare earth metals, one or more isotopes, autologous mitochondria, etc. In general, the additive(s) will not react with or change the properties of the biological sample, or affect generation of a corresponding therapeutic based on the biological sample.

For example, when a biological sample is collected from a patient, one or more additives may be added to the container comprising the biological sample (e.g., additives may be added to a blood sample, a tissue sample, a solid sample, a sample immersed in or mixed with a solution, etc.) to facilitate tracking of the biological sample relative to the container and/or the patient. The number of additives (e.g., number of rare earth metals, number of isotopes, number of monoclonal antibodies, number and/or length of primers, etc.) may be determined based on the total number of patient vials for which tracking is desired. For example, if during a given time frame (e.g., a month, a quarter, a year, etc.), a manufacturing facility or laboratory receives a given number of biological samples for processing (e.g., 5,000 samples, 10,000 samples, 20,000 samples, 100,000 samples, etc.) then the number of additives may scale based on the number of samples being processed within this time frame.

As a specific example, if 20,000 samples are estimated to be processed in a given time frame, then the number of additives that should be added for a unique signature may be determined by $r!(n-r!)$ where r is the number of additives, and n is the total available space of the additives. For twenty different monoclonal antibodies that are approved for use by the FDA, any six of these twenty monoclonal antibodies may be added to the biological sample to generate a unique signature. Selecting any six antibodies of a total of twenty possible antibodies (and assuming the same antibody is not selected more than once) generates 38,760 different antibody signatures. On the other hand, selecting any five antibodies of a total of twenty possible antibodies (and assuming the same antibody is not selected more than once) only generates 15,504 different antibody signatures, which is not sufficient to uniquely cover the total number of estimated samples.

In some cases, the total number of possible combinations (combinatorial space) of a set of additives may not be large enough to cover millions of biological samples. In this case, location specific identifiers may be added to or otherwise associated with the container such that each point of care facility is associated with a unique location specific identifier, thus, linking the vial to the point of care facility. This location dependent identifier may also effectively route therapeutic samples from a manufacturing facility back to the point of care from which the biological sample was obtained. The location dependent identifier may be a bar code, series of digits, QR code, zip code, or any other suitable location specific identifier that effectively expands the combinatorial space of the set of additives, allowing the biological sample to be uniquely identified. In some cases, the vial or container may be manufactured with the location specific identifier on the surface of the container or vial. For example, two biological samples may each have a combination of monoclonal antibody additives (e.g., Erbitux®, Reopro®, Herceptin®, and Remicade®), but may originate from different locations (e.g., a first cancer treatment center associated with a first hospital and a second cancer treatment center associated with a second hospital). By appending or otherwise associating a location specific identifier (e.g., in the case of a zip code, 2128 for the first hospital and 90095 with the second hospital), the identity of the biological sample/therapeutic may be verified.

As indicated previously, monoclonal antibodies, isotopes, heavy metals, primers, etc. may be used as additives to the container or vial in which the biological sample or therapeutic is placed. The sample may be assayed at the manufacturing facility or at the point of care facility to validate the presence of a particular biological sample in a container.

For detection of monoclonal antibodies, any suitable assay may be used, including enzyme linked immunoabsorbant assays (ELISAs). The added monoclonal antibody may bind to its respective antigen bound to a solid support. An anti-IgG antibody may be added that binds to the monoclonal antibody, wherein the anti-IgG antibody is attached to an indicator molecule allowing detection.

In other aspects, monoclonal antibodies may be detected using lateral flow assays. Lateral flow assays are known in the art (e.g., Koczula et al., Essays Biochem (2016) 60(1): 111-120, and Gwyn et al., J. of Immunological Methods (2016) 435: 27). For example, antigens to the respective monoclonal antibodies may be conjugated to gold, and both gold-conjugated and unlabeled antigens may be placed on separate bands of a lateral flow strip. The monoclonal antibodies may migrate up the lateral flow strip, where the antibodies bind to their respective gold conjugated antigens. The antibodies continue to migrate up the lateral flow test strip, and when reaching a test line comprising unlabeled antigens, the monoclonal antibodies bind to the unlabeled antigens on the test line, thereby depositing the gold-conjugated antigens to produce a visible line (e.g., due to the accumulation of gold particles) indicating detection of the antibody.

In other aspects, antigens may be added to the container or vial comprising the biological sample or therapeutic. The antigens may be subjected to a lateral flow test, in which the antigens bind to respective antibodies affixed to the lateral flow test strip. The antibodies may be conjugated to any suitable coloured or fluorescent particle, e.g., colloidal gold or latex microspheres. The antigen, along with the labeled conjugated antibody, migrates along the lateral flow strip until reaching a test zone, where unlabeled immobilized antigen is present. In some aspects, the test zone may be a porous membrane made of nitrocellulose with antigens immobilized in successive lines. Thus, by binding to immobilized antigen, the labeled conjugated antibody may be detected, (e.g., by detection of a visible line) allowing recognition of the sample antigen.

For example, a combination of approved monoclonal antibodies may be added to the biological sample. The vial or container in which the biological sample is placed may be transported to a manufacturing facility. At the manufacturing facility, the contents of the vial may be assayed for the presence of the monoclonal antibodies. The assay may include any suitable technique. Once verified, a suitable therapeutic may be generated based on the biological sample or analysis of the biological sample. The therapeutic may be labeled with the same additive or combination of additives (or a different additive or combination of additives), and sent back to the point of care facility for administration. Prior to administration to the patient, the contents of the container may again be assayed for the presence of specific monoclonal antibodies, in order to verify that the therapeutic within the container is specific to the patient to which it is to be administered.

In other examples, combinations of rare earth metals or isotopes may be added to the biological sample or therapeutic. Rare earth metals may include neodymium (Nd), yttrium (Y), dysprosium (Dy), lanthanum (La), europium (Eu), terbium (Tb), cerium (Ce), praseodymium (Pr), scandium (Sc), lutetium (Lu), gadolinium (Gd), ytterbium (Yb), samarium (Sm), erbium (Er), thulium (Tm), holmium (Ho) and promethium (Pm). For detection of rare earth metals or isotopes, any suitable assay may be used, including mass spectrometry (e.g., inductively coupled plasma—mass spectrometry (ICP-MS)). For example, ICP-MS may be used for the detection of rare earth metals as low as one part per trillion. Such techniques separate ions by their mass to charge ratio, allowing the detection of different isotopes.

In still other aspects, one or more primers may be added to the biological sample or therapeutic. The primers may be assayed (e.g., detection using a DNA hybridization assay) prior to analysis and generation of a patient-specific therapeutic. Additionally, the same one or more primers may be added during one or more processing steps of production of the therapeutic and/or placement of the therapeutic into a container to send to the point of care for administration to the patient. At the time of administration, the primers may be assayed to verify that the therapeutic within the container is the correct therapeutic to be administered to the patient.

In yet another embodiment, DNA barcodes may be placed on the outside of the container to indicate the specific primers that are present in the biological sample or in the therapeutic. Complementary primers may be manufactured based on the DNA barcode, and used to detect the presence of the added primers. For example, a primer having a sequence of "GATCGTCAA" may be represented by a color coded sequence of lines in which red represents "G", green represents "A", yellow represents "C" and blue represents "T". Any suitable color combination in any suitable arrangement may be used. If the primer is not detected, the therapeutic may not be administered to the patient.

Thus, once receiving the labeled biological sample 130 (1), a manufacturing facility or laboratory can assay the contents of the tube to confirm that the biological sample contains the appropriate number of additives. The information obtained from verification of the biological sample may be used to initiate a sample tracking chain (e.g., starting with production block 260-0, and continuing through the production of the therapeutic). Likewise, once receiving the labeled therapeutic 160(1), a point of care facility can assay the contents of the vial to confirm the presence of the therapeutic.

Additives may be added to the biological sample for tracking of the biological sample from the point of care to the manufacturing facility. Additives may also be added during one or more steps of manufacturing of the therapeutic. Additives may additionally be added for tracking the therapeutic from the manufacturing facility to the point of care. In some aspects, a database may be used to track the additives added to a particular container. For example, the vial may have a bar code that when scanned, retrieves a database record listing the additives. In other cases, the additives may be listed on the vial itself. Thus, the assay results may be compared to the information on the label of the vial or associated with the vial.

The biological sample/therapeutic may be assayed at any step in the process to confirm the presence of the material present within the vial. For example, the biological sample may be assayed for the presence of additives at receipt of the manufacturing facility, or during any manufacturing step to generate the therapeutic. At the time of administration, the additives may be assayed to verify that the therapeutic within the container is the correct therapeutic to be administered to the patient.

In general, extrinsic data is information that is not inherent to the object or person, such as an identification number, an address, or other label. In general, intrinsic data is information that is inherent to a person or object, such as a material property, an appearance/phenotype, or a biological sequence corresponding to the individual or object.

Also contemplated herein are compositions of matter including patient-specific compositions of matter and/or corresponding articles of manufacture. For example, a patient-specific composition may include a biological sample from the patient and one or more additives. In other aspects, a patient-specific composition may include the therapeutic produced for a specific patient and one or more additives. In some cases, the patient-specific biological sample or therapeutic may be placed in a vial/container and associated with information comprising one or more of extrinsic patient data, intrinsic patient data, intrinsic biological sample data, extrinsic biological sample data, extrinsic manufacturing data or intrinsic manufacturing data.

Figure 2B:
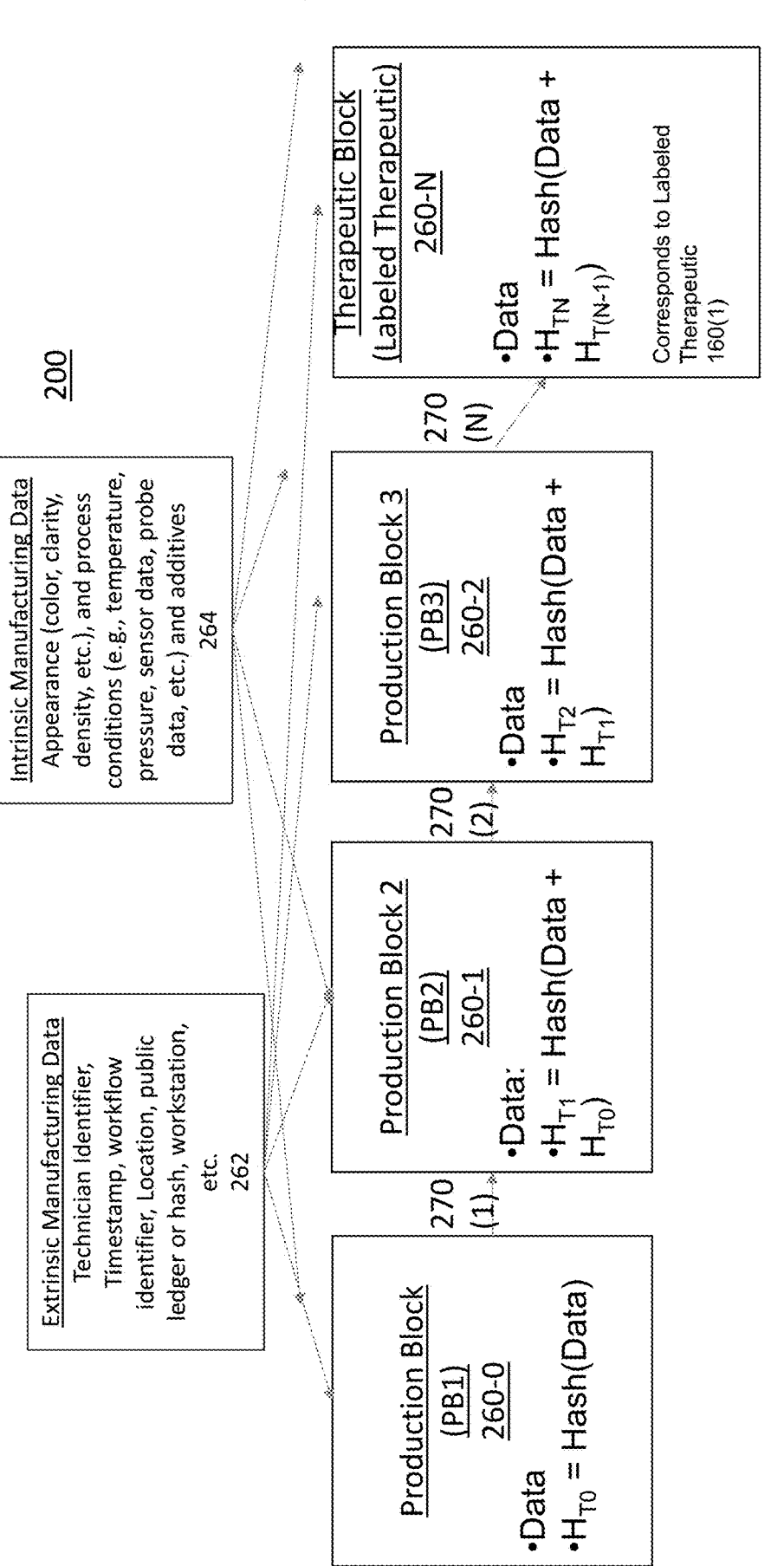

FIG. 2B shows generation of a sample tracking chain for a biological sample from receipt at an analysis/production facility through generation of a labeled therapeutic for a specific individual. Production block 260-0, a genesis block, may be instantiated upon receipt of the biological sample, e.g., zero state ($T_0$; $t=0$), and may include any of data 210-240 that is associated with the biological sample. Production block 260-0 may also include a block token that is generated as a function of any of data 210-240, which may be used to identify production block PB1 260-0. In some embodiments, the block token may be a hash digest ($H_{T0}$) generated according to an implementation of a hash algorithm and as a function of any of data 210-240. In some aspects, a user may verify that the data within production block 260-0 is valid by re-calculating $H_{T0}$ from the available data 210-240. If the data 210-240 in production block 260-0 is altered, the re-calculated hash will differ from the value stored in production block 260-0, thereby allowing the change to be detected. In some aspects, the external hash is generated using a publically available external hash that is associated with a particular timestamp corresponding to the date of public release of the external hash. This allows a partial validation of the timestamp associated with production block PB1. For example, a publically available hash available in March 2018 would validate a timestamp after the release date of the hash (e.g., a block token created using this hash on or after March 2018).

Numerous algorithms are available to generate a block token ($H_{T0}$, $H_{T1}$, $H_{T2}$ . . . $H_{TN}$) for a production block, including but not limited to MD5, SHA (e.g., SHA-1, SHA-2, SHA-3, SHA-256, SHA-512, etc.), Whirlpool, BLAKE2, scrypt, or other suitable hashing functions. In general, secure hash functions (e.g., SHA-1) are able to protect the sample tracking chain from tampering. In other aspects, hash functions generating larger digests (i.e., the hash value) are able to provide unique hashes, allowing co-processing of large sets of biological samples by ensuring that each biological sample has a unique block token associated with it throughout production into a corresponding therapeutic. For example, SHA-512 produces a larger digest than SHA-256 and may accommodate a larger set of biological samples than SHA-256. Other types of functions that may be used to generate a block token include UUID generation functions (e.g., RFC 4122, etc.), GUID generation functions, other types of identifier generation functions, or non-hash-based functions.

Once production block PB1 260-0 is generated, including $H_{T0}$, this information may be provided to production block 2 PB2 260-1, along with extrinsic and intrinsic manufacturing data to generate the next block in the sample tracking chain. For example, extrinsic manufacturing data 262 may include information about the manufacturing process (not including the content of the vial or appearance of the vial in which the biological sample or therapeutic is placed) including the technician identifier, the date, the location, workflow, public ledger, etc.). In some aspects, one or more additives may also be added at each step during the manufacturing process, and captured in each production block, to ensure that manufacturing steps are not skipped and that samples are not mixed up during manufacturing. Thus, the entire production run may be validated using these techniques. In some aspects, rare earth elements or other molecules (e.g., antigens, monoclonal antibodies, primers, isotopes, nanoparticles, fluorescent dyes, etc.) may be added to the biological sample at the end of each processing step. In some aspects, additives are added at a sufficiently high concentration so that the additives are detectable at the end of production. In general, the additives do not react with the biological sample or interfere with processing steps to convert the biological sample into a personalized therapeutic. In other aspects, one or more additives may be added for a subset of steps during the manufacturing process, and captured in each production block, to ensure that samples are not mixed up during manufacturing.

Intrinsic manufacturing data 264 may also be used to generate block ($H_{T1}$). Intrinsic manufacturing data may include but is not limited to appearance of the sample (e.g., color, clarity, density, etc.) or contents of the vial, including reagent(s) added to the biological sample and/or process conditions (e.g., temperature, pressure, sensor data, probe data, viscosity, etc.), and additives. Once the data associated with the next state, state $T_1$, is compiled, the corresponding block token ($H_{T1}$) may be generated and linked to the previous state $T_0$ via one or more links. This process may be repeated for each block in the sample tracking chain, until reaching the finished therapeutic at block 260-N.

In some embodiments, each block 260-0-260-N may be stored as an individual record in a data store or database. In other embodiments, blocks 260-0 and 260-1 form a linked list or a double linked list such that each block points to the other. Links 270(1)-270(N) may have a value corresponding to the identifier of the previous block (e.g., link 270(1) may contain an identifier for block 260-0 and so forth).

In other embodiments, a link may comprise a linked hash digest forming a blockchain where a current biological sample state object "links" back to a previous sample state object via a hash digest generated based on the previous state's block token and the current state data. For example, data block 260-1 may include a block token (i.e., $H_{T1}$) having the form of a hash digest generated by hashing the data of block 260-1 along with the hash digest of block 260-0 (i.e., $H_{T0}$), wherein the block token is link 270(1). In some embodiments, both a hash-based block token and pointers to neighboring blocks are used.

While block 260-1 may be illustrated as having a compilation of all the data from previous blocks, it is also contemplated that each process step may have its own corresponding block within sample tracking chain 260-N. For example, sample tracking chain 260-3 may have a chain of many smaller blocks. Still in other embodiments, the data may be arranged into other structures such as Merkle trees, binary trees, AVL trees, side chains, hashgraphs, directed acyclic graphs, or other non-linear data structures.

In other embodiments, the biological sample may be divided into multiple samples, wherein each sample is processed with a different process flow. Each process may be tracked using a unique sample tracking chain for each process flow. In other aspects, a set of samples may be processed using the same process flow, with a unique sample tracking chain tied to each process. In some aspects, the data may be compiled (e.g., files, raw data, BLOBs, markup language files, etc.) for incorporation into the next block of the sample tracking chain.

In some aspects, hash digests may be generated using any of data 210, 220, 230, 240, 262, and 264. It should be appreciated that certain steps, stages, or states along the workflow 200 path may be observed via one or more sensors (e.g., digital cameras, microscopes, probes, mass spectrometer, etc.) to generate extrinsic and/or intrinsic manufacturing data of the corresponding state of the biological sample(s). These features can also be used to link back to the previous states (e.g., by incorporation into the hash digest). Finally, in the example shown, a final state is achieved at 260-N, which may be linked back to the previous states thereby forming a production or manufacturing life cycle sample tracking chain or block chain audit trail, covering generation of a personalized therapeutic based on a biological sample.

Figure 2C:
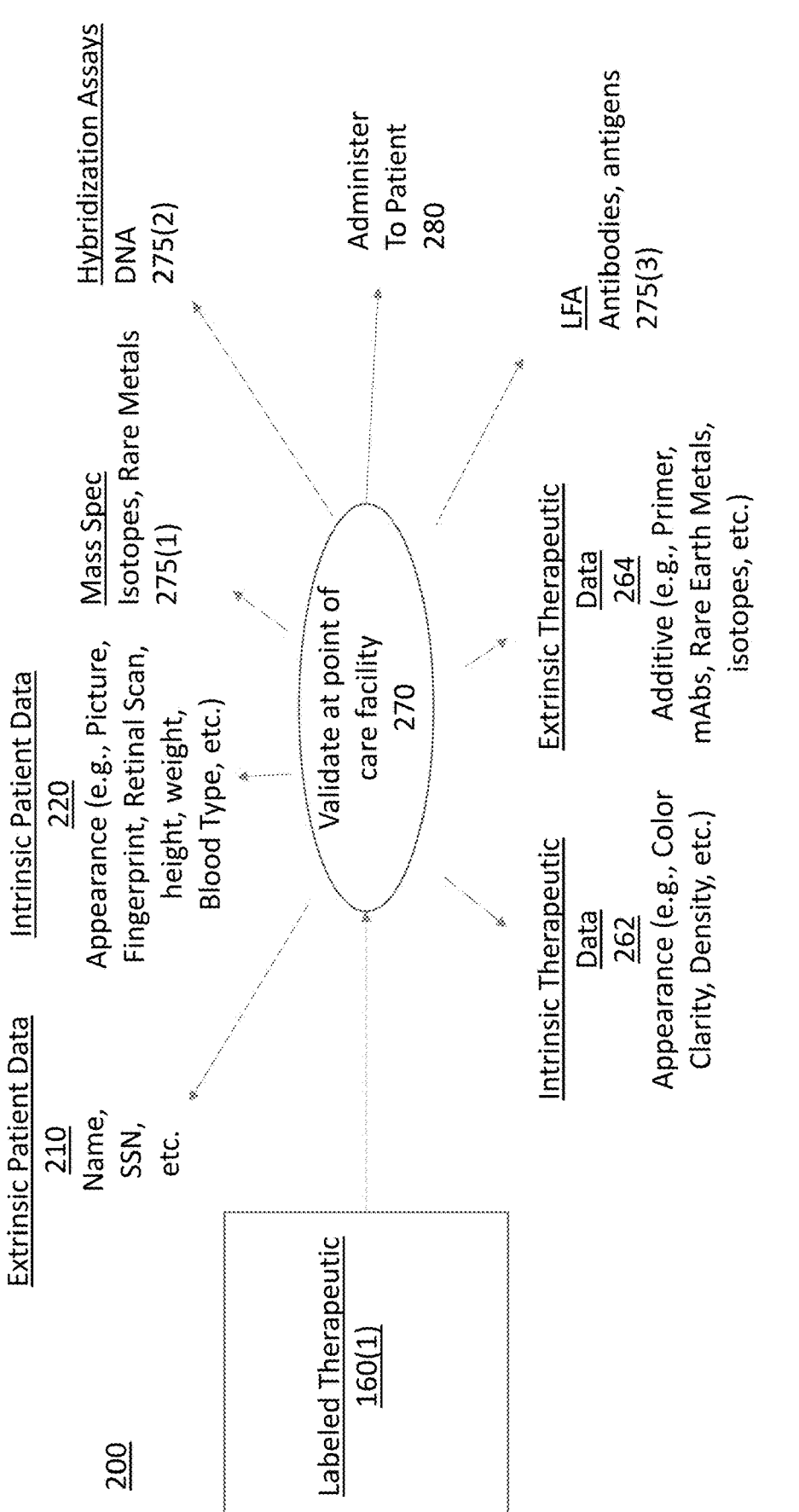

FIG. 2C shows the labeled therapeutic 160(1) being validated at the point of care facility prior to administration to the patient. During manufacturing steps and/or at the end of manufacturing, the therapeutic may be labeled with one or more additives (e.g., isotopes, rare earth metals, primers, antigens, monoclonal antibodies, etc.), such that the additives or combination thereof is unique relative to the therapeutic sample. Once the labeled therapeutic 160(1) is transported from the manufacturing facility to the point of care facility, the labeled therapeutic can be validated for the presence of the additives or combination thereof at operation 270. In some aspects, three validations may be performed.

The last stage in the manufacturing process 260-N corresponds to the labeled therapeutic 160(1). The labeled therapeutic may be associated with extrinsic and/or intrinsic manufacturing data from manufacturing of the personalized therapeutic. Additionally, in some aspects, the extrinsic and intrinsic patient data associated with the biological sample may also be associated with the labeled therapeutic 160(1).

The contents of the vial may be validated. For example, the therapeutic to be administered to the patient may be validated through a lateral flow assay (LFA) in which ELISAs are used to validate the presence of monoclonal antibodies 275(3), by mass spec used to detect isotopes or rare metals 275(1), and/or by hybridization assay used to detect primers 275(2). Information may be associated with the container or included in the labeling of the container, wherein the information lists the isotopes, rare earth metals, antigens, antibodies or primers present in the container, so that the assay results may be compared to the provided information. In some aspects, primers may be labeled on the container in the form of a DNA barcode (and similarly, antigens may be listed as a protein barcode). Fluorescent dyes may be analyzed by spectral analysis.

The identity of the patient may be validated based on extrinsic patient data 210 and intrinsic patient data 220. For example, the information in extrinsic patient data 210 and/or intrinsic patient data 220 may be compared to the patient to which the therapeutic is to be administered. Similarly, the identity of the vial may be validated based on intrinsic manufacturing data 262 and extrinsic manufacturing data 264 (e.g., from 260-N). For example, the information in extrinsic manufacturing data 264 and/or intrinsic manufacturing data 262 may be compared to the vial in which the therapeutic is contained. Once the sample has been validated by one or more of the mechanisms provided herein, the therapeutic may be administered to the patient at operation 280. It is noted that the intrinsic manufacturing data 262 at the last step of production may correspond to intrinsic labeled therapeutic data and that extrinsic manufacturing data 264 at the last step of production may correspond to extrinsic labeled therapeutic data.

Figure 3:
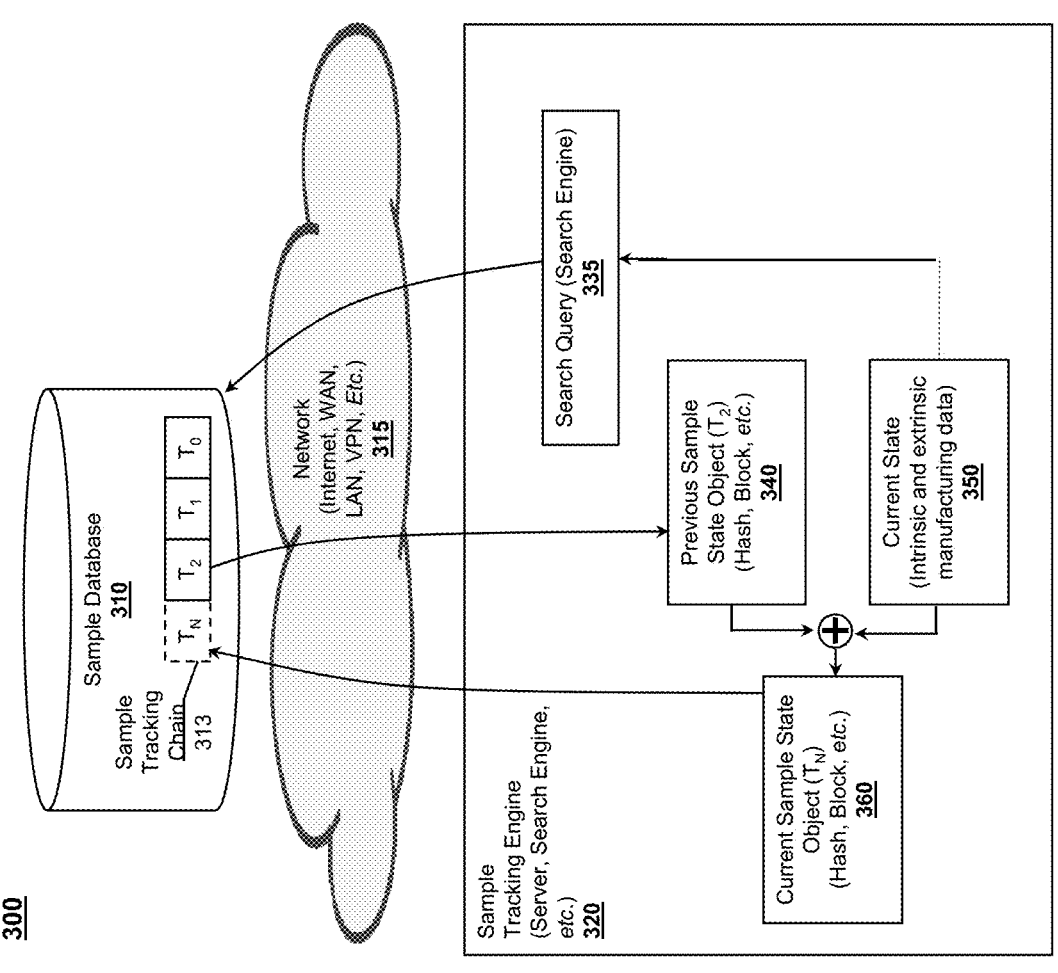
FIG. 3 represents an example flowchart of generating states of a sample tracking chain, according to embodiments of the techniques disclosed herein.

FIG. 3 illustrates sample tracking environment 300 where intrinsic manufacturing properties and extrinsic manufacturing properties may be used to create sample tracking chain 313. Sample tracking chain 313 represents one or more digital data records stored in a computer readable non-transitory memory. Although the process is described with respect to a single user, it should be appreciated that the environment 300 may support tracking of multiple patient-specific therapeutics.

Sample Database 310

A sample database 310 stores one or more sample tracking chains 313, wherein each sample tracking chain 313 represents a manufacturing life cycle or an audit trail of a biological sample, e.g., from receipt at a manufacturing or analysis facility through production of a patient-specific therapeutic. In the example shown, sample tracking chain 313 is stored in the memory of sample database 310; as records in a file system, on a hard disk, or in RAM, for example. Sample database 310 may be configured to retrieve data relating to one or more sample tracking chains 313 based on one or more query criteria (e.g., a patient name, a RF label, a bar code, a hash, a QR identifier, etc.) that may be used to identify and return a particular block chain. Example database technologies that are suitable for use for constructing sample database 310 include but are not limited to MySQL, No SQL, MongoDB, Riak, CouchDB, Open-Cog, ArangoDB, etc. In some aspects, sample tracking chain 313 or its individual state objects may be indexed by the corresponding intrinsic or extrinsic manufacturing properties related to the various states of manufacturing of the therapeutic.

Sample database 310 may be coupled to sample tracking engine 320 to allow sample tracking engine 320 to access the one or more sample tracking chains 313. In some embodiments, as shown, sample tracking engine 320 may be communicatively coupled with sample database 310 over network 315 (e.g., Internet, intranet, WAN, LAN, WLAN, P2P, wireless, cellular, ad-hoc, etc.). Network 315 may include a wireless network (e.g., WUSB, 802.11, 802.15, 802.16, cellular, etc.), a wired network (e.g., Ethernet, circuit switched network, ATM, etc.), or combination of wireless and wired networks. Sample tracking engine 320 may comprise a computing device configured to track a biological sample through an analysis and/or manufacturing process (e.g., generation of a patient-specific therapeutic based on the biological sample).

In some embodiments, sample tracking engine 320 comprises a server system, workstation, tablet, cell phone, or other suitable computing device capable of accessing database 310 locally (e.g., in the same computer, on the same network) or remotely (e.g., over the Internet, WAN, etc.) via a web or other suitable interface (e.g., HTTP, HTTPS, TCP/IP, UDP/IP, etc.). In other embodiments, sample tracking engine 320 may operate as a cloud-based infrastructure (e.g., SaaS, etc.) based on one or more commercially available cloud systems (e.g., Amazon AWS, Microsoft Azure, Google Cloud, etc.).

Sample tracking engine 320 tracks, stores, and/or accesses information related to the labeled biological sample 130(1) during its processing and conversion into a patient-specific therapeutic 160(1). Sample tracking engine 320 may leverage current state 350 in order to track processing of the biological sample into a patient specific therapeutic. For example, sample tracking engine 320 may access one or more of sample tracking chains 313 from sample database 310 where sample tracking chain 313 is stored. For example, sample tracking engine 320 may access the initial block (To) for a particular biological sample and may compile one or more pieces of intrinsic or extrinsic manufacturing data pertaining to analysis or processing of the biological sample to generate current state 350. In some embodiments, current state 350 may include extrinsic manufacturing information (e.g., a technician name, a date, a location, etc.) and/or intrinsic manufacturing information (e.g., appearance of the biological sample or therapeutic, information pertaining to the process conditions, additives, etc.). Extrinsic and intrinsic patient data 210-220 as well as intrinsic and extrinsic biological data 230-240 may also be provided, for inclusion of part or all of this information into the current state 350.

In some aspects, a user (e.g., a manufacturing technician), may provide manufacturing related data to be included as intrinsic or extrinsic manufacturing data at one or more process steps used to generate a current state 350. In other embodiments, a user may add an additive at one or more points in the manufacturing process (e.g., to later verify sample identity via an assay as provided herein or according to the techniques known in the art), and the additive may be provided as data to generate current state 350. Current state 350 may include other modalities of data including information provided by sensors in the manufacturing process.

Sample tracking engine 320 may leverage the compiled information (e.g., intrinsic and extrinsic manufacturing data, intrinsic and extrinsic patient data, intrinsic and extrinsic biological sample data, etc.) as search query terms allowing search engine 335 to access particular sample tracking chains. Typically, the search query is submitted to sample database 310 to return a particular sample tracking chain 313 corresponding to a particular biological sample or therapeutic.

In general, sample tracking engine 320 may retrieve at least one previous sample state object 340 from sample database 310 based on search query 335. Previous sample state object 340 is an instantiated data object, which represents at least one previously recorded state of the labeled biological sample/therapeutic. In this example, the labeled biological sample/therapeutic is illustrated as having three previous states listed as $T_0$, $T_1$, and $T_2$ that represent a state at a previous point in time. Although sample database 310 returns $T_2$ as previous sample state object 340, it should be appreciated that sample database 310 may also return a 'NULL' value indicating that no record yet exists, may return a portion of a matching sample tracking chain 313, or may return the complete sample tracking chain 313. Previous sample state object 340 is not necessarily required to be an immediately preceding state. However, in many embodiments, previous sample state object 340 is an immediately preceding state relative to the data observed in current state 350.

Previous sample state object 340 can be packaged using various techniques. In some embodiments, previous sample state object 340 can be presented to sample tracking engine 320 in its native form; e.g., as a binary record, a file, raw text, or other format by which previous sample state object 340 is stored. In other embodiments, sample database 310 can re-package previous sample state object 340 into a desired format for delivery to sample tracking engine 320. Example formats can include a CSV file, a binary object, a BLOB, a serialized data structure (e.g., YAML, XML, JSON, etc.), or other formats. In some aspects, previous sample state object 340 can include a block token, typically a hash digest, which represents or identifies previous sample state object 340. In some aspects, a hash digest is a bit string of a fixed size, e.g., about 128 to 256 bits in length, or more. A hash function may be used to map data of an arbitrary size to a fixed size hash digest. If one bit of the arbitrary sized data changes, a different digest will be generated by the hash function. Therefore, hash digests are suitable for tracking data integrity as well as other applications as presented herein. In other aspects, a cryptographic function may be used to generate the hash digest.

Sample tracking engine 320 also generates or otherwise instantiates one or more of current state 350, which may be an intermediate data structure stored in the memory of sample tracking engine 320 in preparation of creating a current state object 360. For example, current state 350 may include extrinsic and intrinsic manufacturing data, including digital images, video, audio, sensor, or other forms of data added by a user or obtained or compiled during process steps. With respect to digital images, current state 350 could include one or more descriptors generated according to one or more image processing algorithms. The descriptors could include one or more of the following types of descriptors SIFT, SURF, GLOH, TILT, DAISY, HOG, uncanny edges, corners, blob descriptors, textures, shape descriptors, or other types of descriptors. Current state 350 may also include intrinsic and/or extrinsic patient and/or biological sample data, including bar code information, RFID codes, sample identifiers, name, time stamps, metadata, location, or other types of information.

Once the data associated with current state 350 has been collected, sample tracking engine 320 instantiates current sample state object 360 in memory as a function of current state 350 and previous sample state object 340. When current sample state object 360 is instantiated, it may be initially created having NULL values that are then populated after instantiation. Alternatively, current sample state object 360 can be created having fully fleshed out values by passing data from current state 350 and previous sample state object 340 to the constructor method of current sample state object 360. In some embodiments, current sample state object 360 can also be constructed based on external data, such as a hash digest from one or more external distributed, public ledgers (e.g., BitCoin, LiteCoin, Ethereum, etc.) as form of notorization. According to certain aspects, external data from a public ledger, such as a hash digest associated with BitCoin, can be used as a notary, providing an independent measure of the validity of the timestamp associated with the sample state object. The public ledger data or hash digest acts as an external timestamp that is independent of the sample tracking chain with respect to a particular point of time or a time thereafter. Thus, generating a current sample state object using the public ledger provides an independent validation that the data from the corresponding block has not been tampered with or modified.

In some embodiments, the block of data represented by current sample state object 360 depends directly on the previous state of the biological sample/therapeutic. Thus, a blockchain of intrinsic states may be formed.

Sample tracking engine 320 links current sample state object 360 to previous sample state object 340 to continue building the sample tracking chain. For example, current sample state object 360, labeled as $T_N$, may include data from current state 350 as well as a hash digest generated by hashing data from current state 350 along with a hash digest from the previous sample state object 340. The linking function used to combine or otherwise link the previous sample state object 340 with the current state 350 is shown by the "Circle-Plus" symbol. Once current sample state object 360 has been instantiated and linked, sample tracking engine 320 updates sample tracking chain 313 in sample database 310 with the newly created and linked current sample state object 360. Sample tracking chain 313 may be updated by sample tracking engine 320 sending current sample state object 360, possibly in a serialized format (e.g., XML, YAML, JSON, etc.), to sample database 310 over network 315. Further, sample tracking chain 313 and current sample state object 360 may be indexed by the newly generated intrinsic and/or extrinsic data.

In general, sample tracking chain 313 may be instantiated as a single stand-alone sample tracking chain for a single sample to represent the sample's manufacturing life cycle. Thus, unlike cryptocurrency-based block chain implementations, sample tracking chain 313 may remain self-contained and relatively small without incurring unlimited growth or requiring specialized hardware resources. Further, sample tracking chain 313 does not require a significant amount of work to create a next block, rather sample tracking engine 320 can quickly execute the desired linking function without requiring a solution to a time consuming cryptographic puzzle (e.g., proof of work, a hash digest with a specific signature, etc.).

The sample tracking chain 313 is updated based on a workflow of processing a biological sample into a therapeutic. A workflow may comprise multiple processing steps, with one or more steps in the workflow altering the physical or molecular characteristics of the biological sample to form the therapeutic. Thus, the sample tracking chain provides a way in which to track the biological sample through the entire workflow of producing a corresponding therapeutic, while maintaining a record of physical and/or molecular characteristics at various steps of the workflow. In some approaches, each step of the workflow may be recorded in the sample tracking chain. In other approaches, a subset of steps of the workflow may be recorded in the sample tracking chain. Thus, these techniques are suitable for managing a population of patient samples, at different processing stages of a workflow, to reduce errors occurring from sample mix-ups.

Sample tracking chain 313 and its individual blocks may be indexed using various techniques to provide quick retrieval and/or management using search engine 335. As sample tracking chain 313 comprises many states wherein each state has its own associated intrinsic and extrinsic data, the values or metrics derived from these properties can be used to index sample tracking chain 313 and its corresponding sections. Thus, one or more metrics associated with the physical sample's intrinsic or extrinsic data may be used to retrieve sample tracking chain 313 or portions (e.g., blocks, etc.) thereof.

The present approach is considered superior to the exclusive use of patient information as the properties of the biological sample/therapeutic are linked to the contents of the container, which reduces potential errors generated by mishandling or mislabeling of samples. The techniques presented herein are not limited to this example workflow. In general, the techniques presented herein can be used to track any number of biological samples through one or more steps of a manufacturing workflow to generate a therapeutic for a specific patient. For example, companies providing genetic analysis services could utilize the sample tracking techniques provided herein, to monitor each sample as it is processed (e.g., through various stages of DNA sequencing workflows, RNA sequencing workflows, proteomics analysis workflows, immunoassay workflows, biomarker analysis workflows, purification workflows, or any combination thereof, etc.), to greatly reduce errors arising from manual handling of samples. Additionally, if processing errors or discrepancies are discovered at a later point in time (e.g., from mishandling by a particular technician, from contamination introduced by a particular instrument, from using a defective reagent in manufacturing process, etc.), these techniques can be used to precisely identify which therapeutics of a population of therapeutics have been affected, rather than presuming the entire population has been affected.

Other examples include manufacturing workflows, including large and small scale pharmaceutical and biologic manufacturing, as well as other types of manufacturing processes, etc. Intrinsic and extrinsic properties of a manufacturing process can be tracked as a function of time including large and small scale pharmaceutical and biologic manufacturing processes (e.g., reagents, time of addition of reagents and/or additives, composition of additives, technician, impurities, formation of product, viral or bacterial contamination, formation of side products, etc.).

Sample tracking chain 313 may include data about the biological sample/therapeutic itself. For example, data pertaining to genomic or proteomic sequences (e.g., whole genome sequence, whole exome sequences, known mutations, SNP patterns, RNA-seq data, proteomics, etc.), chemical composition, etc. may be associated with blocks of the sample tracking chain. In other aspects, the data pertaining to genomic or proteomic sequences may be included on the container in which the therapeutic is placed (e.g., for sending back to a point of care facility for administration to a patient).

Sample tracking chain 313 as presented only has four blocks shown representing four states for illustrative purposes and should not be considered limiting. Rather, it should be apparent to the reader that sample tracking chain 313 can include any arbitrarily large number of blocks and/or corresponding states. Such chains can include thousands, millions, or even more blocks depending on the nature of the chain. While sample tracking chain 313 is shown as a single, standalone chain, it may compose larger structures having many other features.

There are numerous techniques available by which sample tracking chain 313 can be instantiated. In some embodiments, sample tracking chain 313 comprises a set of data blocks linked by recursive hash digests, possibly along with pointers. Each block could be stored as a separate record in a database. Other embodiments provide for instantiation of sample tracking chain 313 as a true blockchain, wherein the blockchain may be part of a private ledger. Existing technologies may be adapted for use to create sample tracking chain 313, such as BitCoin, Ethereum (see URL www.ethereum.org), ZCash, or the Hyper Ledger Project (see URL www.hyperledger.org) etc.

In view that the blocks of the blockchain can include patient data, the data can be secured via one or more cryptographic techniques (e.g., 3DES, AES, etc.). For example, the private data stored in the blocks of sample tracking chain 313 can be encrypted based on a private key.

In some embodiments, sample tracking chain 313 may be stored within a graph database. For example, each state or block in sample tracking chain 313 may be stored as a node within the graph database schema wherein the transition from one state to another represents the edge between the nodes. Further, extrinsic and/or intrinsic information can be stored as properties for the nodes and/or edges. Thus, the graph database can be used to retrieve quickly relevant information not just about individual sample tracking chains 313, but also relevant information from collections of sample tracking chains 313 having similar graphs with similar properties. Such an approach is advantageous when storing or analyzing large numbers of manufacturing processes. Example graph database implementations that may be leveraged to store sample tracking chain 313 include Neo4j, OpenCog, and ArangoDB, among others. In some embodiments, graph databases such as OpenCog, which provides an AI framework, might be more desirable when sample tracking chains 313 are coupled to treatments and outcomes of patients. Such a coupling provides a solid foundation for generating automated, reasoned hypotheses about a new patient's possible outcomes based on comparison of the patient's sample tracking chain 313 to previous, known sample tracking chains and outcomes. Example reasoning engines that can be adapted to leverage graph database implementations of sample tracking chain 313 are described in U.S. Pat. No. 9,262,719 to Soon-Shiong titled "Reasoning Engines", filed internationally on Mar. 22, 2012.

One should appreciate that sample tracking chain 313 also provides a solid foundation for compliance with one or more regulations. For example, sample tracking chain 313 may include block-level data that complies with IEC 62304 audit trail requirements, 21 CFR part 11 requirements, HIPPA regulations, HL7 support, or other features.

In general, the methods and techniques provided herein may cover tracking any suitable type of biological sample including saliva, urine, blood, ovum, sperm, stool, skin, sweat, etc.

FIGS. 4A-4B present examples of computer implemented methods for tracking a biological sample. At operation 410, a biological sample from a patient is contacted with one or more additives, wherein the additives uniquely identify the biological sample among a population of biological samples to produce a labeled biological sample. For example, the additives may include monoclonal antibodies, antigens, isotopes, rare earth metals, dyes, primers, or any other suitable material that is stable and will not modify the biological sample or the therapeutic. Monoclonal antibodies that are contacted with the biological sample may be pharmaceutical grade, and in general, approved by a regulatory agency. In general, the one or more additives may be administered to the recipient at a concentration to allow identification without causing deleterious side effects.

At operation 415, a first container is associated with information comprising extrinsic and/or intrinsic patient data to uniquely identify the patient, and extrinsic and/or intrinsic biological sample data to uniquely identify the biological sample, wherein the first container comprises the labeled biological sample. For example, the container may include extrinsic patient data (e.g., name, social security number, etc.) as well as intrinsic patient data describing the appearance of the patient (e.g., a picture, a fingerprint, a retinal scan, etc.) The first container may also include intrinsic information about the biological sample (e.g., color, clarity, density, etc.) as well as extrinsic information about the biological sample, including additives that were mixed with the biological sample. For example, the container may display or be associated with a listing of the types and/or ratio amounts of isotopes, a listing of antibodies, a DNA barcode representing one or more primers, a listing of dyes, etc. In some aspects, the therapeutic (e.g., vaccine) may be validated (e.g., via a mobile device, a portable electronic device, or other computing system) at the point of care by comparing the patient's face, iris, or other biometric features to the labeled therapeutic and information associated with the labeled therapeutic.

At operation 420, the first container is provided to a facility for generation of a labeled therapeutic based on the labeled biological sample. Example processing of the labeled biological sample into a labeled therapeutic is described in FIG. 4B. At operation 425, a second container comprising the labeled therapeutic is received at the point-of-care, wherein the second container displays or is otherwise associated with extrinsic and/or intrinsic patient data to uniquely identify the patient and extrinsic and/or intrinsic therapeutic data to uniquely identify the labeled therapeutic. At 430, the labeled therapeutic is validated by testing for one or more additives which uniquely identify the therapeutic among a population of therapeutics.

The labeled therapeutic may be validated in a variety of different ways. For example, a sample of the labeled therapeutic may be obtained from the container in which the therapeutic is placed. The sample may be tested for the presence of the additive(s) by any of the aforementioned techniques (e.g., mass spectrometry, lateral flow assay, hybridization, colorimetry, etc.). In some aspects, the additives may be identified and compared to identifying information (e.g., pertaining to the types or amounts of additives) on the container or otherwise associated with the therapeutic. For example, the container may include a listing of additives or a label (e.g., a bar code or other tag allowing the list of additives to be retrieved via a database). By detecting or testing for the presence of the additives, and comparing the detected additives with the listing of additives, the identity of the therapeutic may be validated with respect to its container.

The therapeutic vial may also include or be associated with extrinsic or intrinsic patient data or a label (e.g., a bar code or other tag allowing retrieval of the extrinsic or intrinsic patient data in a database). The vial may be validated with respect to the identity of the patient, by comparing information associated with the vial with intrinsic patient data and/or extrinsic patient data, thus validating the vial relative to the identity of the patient.

In some aspects, a fingerprint, an iris scan, or facial recognition technology may be used to identify the patient, and correlate patient identification with the container/vial. In this example, the vial may be labeled with intrinsic or extrinsic patient information at the point of care at which the biological sample is obtained. This label or association may persist throughout the manufacturing process, and may be used to validate the therapeutic prior to administration to the patient. For example, a first set of information (e.g., a fingerprint, iris scan or photo of the patient) may be taken at the point of care and associated with the vial containing the biological sample throughout the manufacturing process of generating a patient-specific therapeutic. Once the labeled therapeutic is received at the point of care, a second set of information (e.g., a fingerprint, iris scan or photo of the patient) may be obtained and compared to the first set of information associated with the vial containing the therapeutic. If the two sets of information match, then the identity of the patient with respect to the vial is validated. Any suitable software may be used to compare the sets of information, including fingerprint recognition software, iris recognition software, and/or facial recognition software.

In other aspects, additives may be added to the vial at the point of care at which the biological sample is obtained. The additives may be linked to patient intrinsic or extrinsic data in a database. In this example, the identity of the one or more additives may be provided to the manufacturing facility. The manufacturing facility may include a new set of additives or may maintain the same set of additives. The additives may be added to the therapeutic container containing the therapeutic (or added during manufacture of the therapeutic), and the container may be sent back to the point of care for administration of the therapeutic to the patient. The additives may be linked in the database to the identity of the patient, which can be validated via a fingerprint, iris scan, facial recognition technology or other biometric parameter(s), prior to administration of the therapeutic to the patient.

In some aspects, the container in which the biological sample and/or therapeutic is placed may comprise two sets of unique additives in vials or capsules associated with or contained within the container (e.g., as a kit), such that the two sets of unique additives are associated with a specific patient via a database. The first set of unique additives may be added to the biological sample at the point of care, and the second set of unique additives may be added to the therapeutic at the manufacturing facility. The two sets of additives may be composed of the same types of additives or different types of additives. When the labeled therapeutic arrives at the point of care, the therapeutic may be assayed for the presence of the second set of additives, to validate that the correct therapeutic is in the correct container (and is being administered to the correct patient). Thus, kits may be provided that include a vial and two sets of unique additives, wherein the number of additives in the sets of unique additives are determined by the size of the patient population.

The vial or container in which the therapeutic is placed may be tamper proof. For example, in some aspects, the vial may be sealed, such that once the vial is opened, the vial cannot be resealed.

In some embodiments, the testing results may be compared to information on the container, which identifies the additives and/or their respective ratios to each other. In other embodiments, the testing results may be compared to information in a database, retrieved by labels or other identifiers on the second container, which identifies the additives and/or their respective ratios to each other. At operation 435, upon validation of the labeled therapeutic (e.g., validating that the labeled therapeutic in the vial is for administration to the patient), the labeled therapeutic is administered to the patient. Accordingly, the identity of the patient is tied to the container and the identity of the biological sample is tied to the container, allowing multi-point validation.

FIG. 4B presents an example computer implemented method of tracking generation of a labeled therapeutic, based on a labeled biological sample. In this workflow, a labeled biological sample is received at a manufacturing facility. In some embodiments, the labeled biological sample may be analyzed, and the results of the analysis used to generate the labeled therapeutic. In other embodiments, the labeled biological material may serve as the starting material for the labeled therapeutic. A variety of scenarios are contemplated, with each scenario leading to generation of a patient-specific therapeutic, either directly or indirectly from the labeled biological sample and/or based on analysis of the labeled biological sample. The steps of this method may be executed by one or more processors according to software instructions stored in a non-transitory computer readable memory. Example computing devices that can be configured to operate as a sample tracking engine or as a search engine according to this method include cell phones, web servers, work stations, tablet computers, cloud-based servers, or other computing devices having access to manufacturing and process information for generation of the labeled therapeutic.

At operation 440, a first container comprising a labeled biological sample is received. At operation 445, the labeled biological sample may be validated by testing for the presence of one or more additives that uniquely identify the labeled biological sample among a population of labeled biological samples.

At operation 450, an initial block of a sample tracking chain is generated, based upon extrinsic and/or intrinsic patient data, which uniquely identifies the patient, and extrinsic and/or intrinsic biological sample data, which uniquely identifies the labeled biological sample. The initial block represents the initial state of the labeled biological sample typically at receipt at the manufacturing facility. Example intrinsic biological sample data may include aspects of the appearance of the sample (e.g., sample mass, shape, sample type, dielectric properties, mechanical properties, acoustic properties, color, clarity, density, elasticity, or any other intrinsic properties of the sample). Extrinsic biological sample data may include characteristics (e.g., type, quantity, ratio, etc.) of the additives mixed with the biological sample to generate the labeled biological sample. Extrinsic patient data may include traditional data to identify the patient (e.g., name, address, phone number, etc.). Intrinsic patient data may include aspects of the appearance of the patient (e.g., photo ID, fingerprint, retinal scan, height, weight, blood type, etc.).

In typical embodiments, the donor is a human patient. However, the donor could also be an animal or other type of living organism. External patient data may also include a hash value or digest obtained from data including an apriori existing external distributed public ledger (e.g., BitCoin, Ethereum, HyperLedger, etc.). The external hash digest provides an authoritative and verifiable marker or token indicating that the biological sample was taken after a specific point in time. Once the data associated with the initial block of the sample tracking chain is compiled, this data (e.g., intrinsic and/or extrinsic biological sample data, intrinsic and/or extrinsic patient data, etc.) is used to generate an initial block token that substantially identifies the initial block. In some embodiments, the initial block token comprises a hash digest of the initial block's data where the hash digest is generated according to one or more implementations of a hash algorithm. Once the initial block is instantiated, it may be stored in a database or other storage system indexed by extrinsic and/or intrinsic patient data and intrinsic and/or extrinsic biological sample data. The initial block becomes the first block of the sample's corresponding sample tracking chain that chronicles generation of the patient-specific therapeutic corresponding to the labeled biological sample. In some aspects, this chronicle may also provide an audit trail for the patient-specific biological sample/patient-specific therapeutic. The hash digest may be stored locally, for comparison to a regenerated hash digest using the same data at a later point in time. In this case, both hash values should be identical, and therefore, may be used to verify the integrity of the initial block.

Operation 455 involves generating a sample tracking chain to reflect manufacturing or processing steps for generating the labeled therapeutic. A search engine may be utilized to access the initial block, and once the initial block is located, the sample tracking chain may be updated with new sample state information based on intrinsic manufacturing. Operation 455 includes a device (e.g., sample tracking engine, sample search engine, etc.) obtaining access to the sample tracking chain of the labeled therapeutic, and in some scenarios, the digital representation may include raw sensor data obtained from extrinsic and intrinsic and/or extrinsic manufacturing data associated with a step of the manufacturing process. The extrinsic and/or intrinsic manufacturing data may be compiled into a query (e.g., SQL command, keywords, look-up indices, etc.), for submission into the sample database storing one or more patient-specific labeled therapeutic sample tracking chains. The disclosed approach may reduce false positives by relying on intrinsic and/or extrinsic features of the biological/therapeutic sample, including verification of one or more additives, providing an improvement over error-prone manual processes. The therapeutic may be labeled during any one or more steps of the manufacturing process and/or at the completion of the manufacturing process.

It is understood that one or more additives may be mixed with the therapeutic (e.g., once during the manufacturing process, at each step of the manufacturing processing, or during selected steps of the manufacturing process, at the beginning of the manufacturing process, at the end of the manufacturing process, etc.), and that theses additives uniquely identify the patient-specific therapeutic from other therapeutics being generated within a given timeframe.

Operation 460 retrieves a previous sample state object from the sample tracking chain, wherein the previous sample state object includes at least one portion of the sample tracking chain that has data representing a previous state of manufacturing of the labeled therapeutic. In some aspects, the previous sample state object can be a block of data from a blockchain. The block, as discussed with respect to FIG. 3, may include one or more block tokens that identify the block and is generated as a function of the block's data along with previous state information, such as a hash digest from a previous block. The previous sample state object is used as a foundation for creating a new block, and in typical embodiments, the previous sample state object is an immediately preceding block. However, it is also contemplated that the previous sample state object may correspond to any previous state of manufacturing of the therapeutic/biological sample or may even be a complete blockchain associated with the labeled therapeutic.

Operation 470 includes generating a current sample state object corresponding to manufacturing of the labeled therapeutic (e.g., a manufacturing step). In some aspects, a current state may be generated based on extrinsic and/or intrinsic manufacturing data (e.g., comprising the raw data or data files associated with the one or more sensors or other data sources that represent the characteristics of the labeled therapeutic at a particular point in the manufacturing process). The term "current state" may refer to intermediary data objects related to the therapeutic in preparation for creating a corresponding complete block object. Operation 470, which creates a new block object for integration into the sample tracking chain, may comprise deriving a current sample state object as a function of the current state, wherein the current sample state object represents a fully instantiated block of data that can be integrated within the sample tracking chain for the labeled therapeutic. Typically, the current sample state object includes intrinsic and extrinsic manufacturing data that represents the therapeutic. The current sample state object may also include a block token, a hash digest for example, which is generated from current data as well as a block token from the previous sample state object. For example, at operation 470, generating the block token for the current sample state object may include calculating a hash digest for the current sample state object based on the previous state's hash digest. In some aspects, a hash digest can be a concatenation of the previous state's hash and the current state data. In other aspects, a hash digest can be a combination of the previous state's hash and the current state data.

In general, the hash digest may include multiple iterations of the same hash function (e.g., SHA-512(SHA-512(data))) or a heterogeneous mix of hash functions (e.g., SHA-512 (scrypt(data))) to reduce hash collisions.

Operation 475 includes linking the current sample state object to the previous sample state object in the sample tracking chain. In some embodiments, generating a hash digest from the previous sample state object forms the link. In other embodiments, the newly created or instantiated block may include a pointer back to the previous sample state object, or the previous sample state object can be updated with a pointer that points to the newly created current sample state object thereby forming a double linked list where each block links to its neighbors.

Operation 480 includes updating the sample tracking chain with the current sample state object. Depending on the implementation, this step can take on different characteristics. In a linked list-based system, the current sample state object can be stored in a database and the previous sample state object can be updated with a pointer. Still, in other blockchain embodiments, the sample tracking chain may be updated to incorporate the block representing the current sample state object wherein the sample tracking chain is a single record.

At operation 485, if the end of the manufacturing process is reached, the workflow proceeds to operation 490. During the process of manufacturing, one or more additives may be added at any step or combination of steps to uniquely identify the labeled therapeutic. In some cases, this may be performed as part of the last step in the manufacturing process. In other cases, a different additive may be added at each step in the manufacturing process to verify that all processing steps were performed. In other embodiments, one or more additives may be added for a subset of processing steps. The labeled therapeutic may be transferred to a second container for sending to the point of care facility for validation and administration to a patient. The second container may be labeled with or be associated with extrinsic and/or intrinsic patient data to uniquely identify the patient and extrinsic and/or intrinsic manufacturing data to uniquely identify the labeled therapeutic.

On the other hand, if another manufacturing process step is to be performed, the work flow progresses to operation 455, to repeat generation of another block of the sample tracking chain. Of course, at any step during manufacturing, one or more additives may be added to uniquely identify the therapeutic.

As discussed previously, indexing the sample tracking chain as well as the current sample state objects based on extrinsic and/or intrinsic data enables fast and valid retrieval of data pertaining to the therapeutic.

The sample tracking chain can continue to grow according to one or more of the steps described above as desired. The resulting tracking chain has numerous clear technical benefits. First, the life cycle of the patient-specific therapeutic is chronicled and can be quickly retrieved via a computing device based on the extrinsic and/or intrinsic features that are used to form a digital index of the sample at each stage (or more or less frequently) of manufacturing. Second, the sample data can be validated by using a computing device to re-calculate the various block tokens in the chain. Further, one can validate that the data was in existence by certain times based on external hash digests from existing, external public ledgers.

Also, the present techniques provide multipoint validation: (1) the relationship of the patient to the vial may be validated, (2) the relationship of the vial to the labeled biological sample may be validated, (3) and the relationship of the labeled therapeutic to the patient may be validated. Additionally, the techniques presented herein may be used to validate that particular steps of the manufacturing process are performed, helping to ensure that the manufacturing is performed according to protocols. Present techniques thus greatly reduce the possibility of accidental mix-ups, and provide a robust method of validating that the patient-specific therapeutics are administered to the proper patient.

In some embodiments, the sample tracking chain can be a standalone data structure, e.g., an individual data structure. In other embodiments, the sample tracking chain can be part of a larger block chain infrastructure, e.g., as part of a hyper ledger or other block chain based infrastructure, or integrated into other existing sample tracking chains or block chains. In other embodiments, the sample tracking chain can be part of a larger block chain infrastructure, e.g., associated with a technician or a facility, etc. Examples of storing healthcare data in a large block chain to create a healthcare historical blockchain (IHHBC) may be found in U.S. patent application Ser. No. 14/711,740, which is incorporated by reference herein.

To facilitate identification of relevant data, the sample tracking chain may also include metadata. Various types of metadata can be collected and incorporated into the sample state object to describe the characteristics of the sample. The database can be used to store various types of metadata used to characterize the sample and/or to facilitate identification of data of interest.

The examples presented herein refer to different subcategories of patient data, such as intrinsic patient data and extrinsic patient data. Similarly, the examples refer to categories of manufacturing data (e.g., extrinsic manufacturing data and intrinsic manufacturing data) and biological sample data (intrinsic biological sample data and extrinsic biological sample data). However, the present techniques may also be generally applied to patient data, manufacturing data, and biological sample data, without further dividing into subcategories.

Figures 5A, 5B:
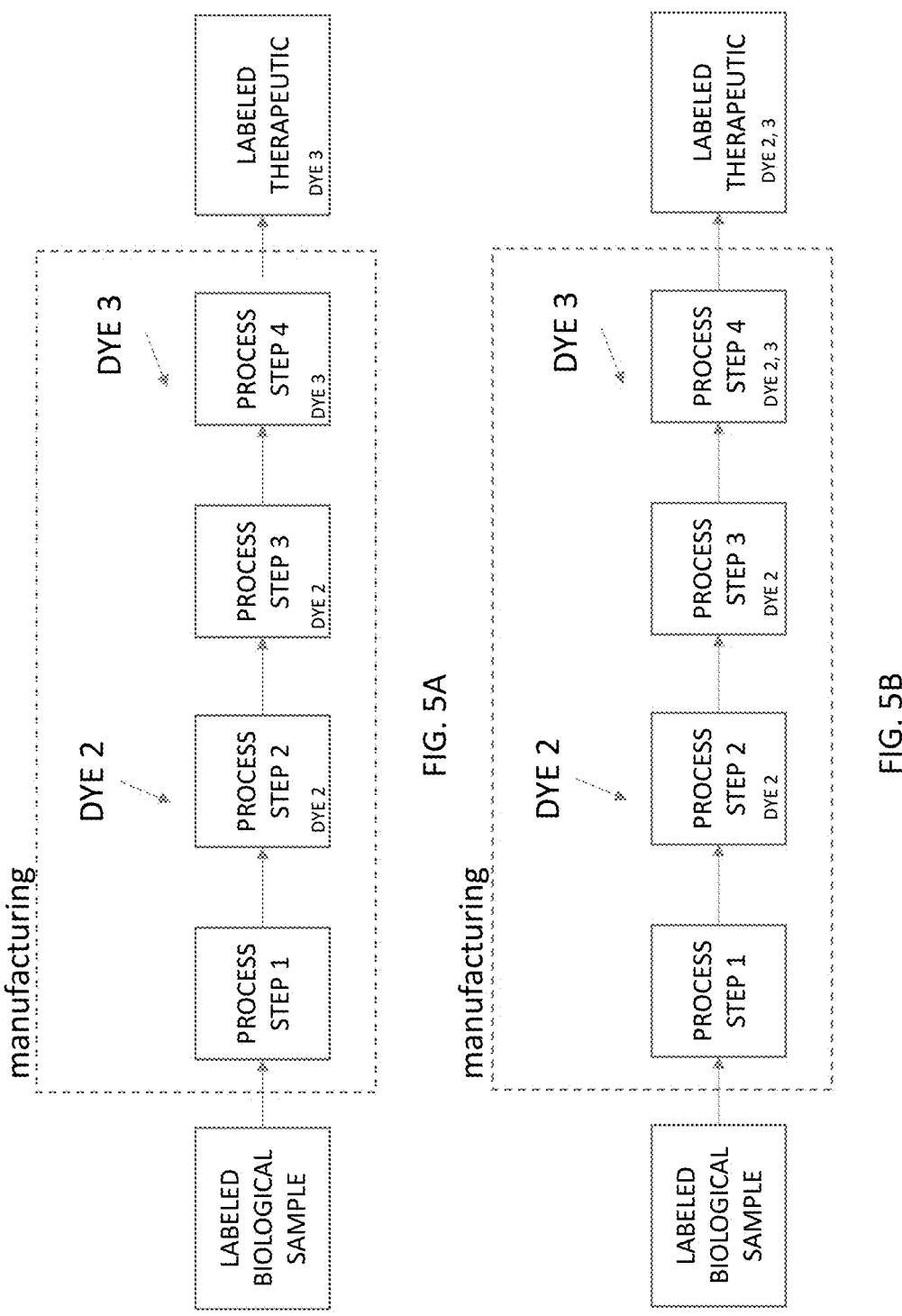
FIGS. 5A-5B present example workflows using additives (e.g., monoclonal antibodies, trace heavy metals, dyes, or added primers, etc.), according to embodiments of the techniques disclosed herein.

FIGS. 5A and 5B show example workflows of labeling a therapeutic. In FIG. 5A, a labeled biological sample is received. The biological sample is used to generate a therapeutic, using a manufacturing process with four process steps. At process step 2, dye 2 is added. Any number of dyes may be added at any one or more process steps. The presence of dye 2 may be tested for at process step 3 for validation. Process step 3 may then undergo a processing step involving dilution or washing of the therapeutic material. Thus, dye 2 may be diluted to an extent that it is no longer detectable. Another label, dye 3, may be added at process step 4. The labeled therapeutic may be shipped to the patient, and assayed for the presence of dye 3 prior to administration to the patient.

In FIG. 5B, a labeled biological sample is received. The labeled biological sample is used to generate a labeled therapeutic, using a manufacturing process with four process steps. At process step 2, dye 2 is added. The presence of the dye 2 may be tested for at process step 3. Process step 3 may undergo an additional processing step while retaining dye 2 at a concentration that is still detectable. Another label, dye 3, may be added at process step 4. The labeled therapeutic may be shipped to the patient, and assayed for the presence of dyes 2 and 3 prior to administration to the patient.

Present techniques may be used for any suitable application, including manufacture of patient-specific therapeutics, patient-specific biologics, patient-specific viral vaccines, etc. In some embodiments, a barcode may be associated with the patient-specific viral vaccine(s). For example, DNA sequences (e.g., DNA barcodes) may be used to identify the virus.

In some aspects, intrinsic data from a patient (e.g., a fingerprint, a retinal scan, facial recognition, etc.) may be used as a key to decipher an encrypted message associated with a patient's point of care. For example, an algorithm (SIFT) may analyze an image of a patient. The SIFT descriptors (129 bytes) can be converted to one or more vocabulary words (e.g., 3 bytes). The collection of SIFT descriptors can then be hashed together to form a key, and the key can be used to unlock the patient-specific message. In some embodiments, the message may include a vial ID that needs to match the identifier on the vial in the doctor's hand in order to authenticate for administration to the patient.

In general, intrinsic and/or extrinsic patient data will be used to form the initial block of a sample tracking chain, as well as be used for validation at the point of care.

In still other embodiments, intrinsic patient data such as patient volatiles may be obtained along with the biological sample and used for validation of the labeled therapeutic at the point of care. For example, a first DNA sample of the patient may be collected (e.g., using a swab) and analyzed when the biological sample is obtained. After manufacturing of the labeled therapeutic, the labeled therapeutic may be linked to the first DNA sequence(s) of the patient. Prior to administration of the labeled therapeutic to the patient, the patient may be swabbed again to obtain a second DNA sample, and the second DNA sample may be analyzed and compared to the first DNA sample for validation.

In still other embodiments, the labeled therapeutic may arrive in a double vial having a jacket, with a tagged substance and an internal vial that contains the vaccine. The tagged substance may be validated prior to administration of the vaccine to the patient.

It should be apparent to those skilled in the art that many more modifications besides those already described are possible without departing from the concepts presented herein. The disclosed subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A method of tracking a labeled biological sample through a manufacturing process, the method comprising:
   receiving the labeled biological sample at a manufacturing facility, wherein the biological sample is labeled with one or more first additives by inserting the one or more first additives into a container comprising the biological sample, wherein the one or more first additives uniquely label the biological sample among a population of biological samples, and wherein the one or more first additives include at least one of a primer, a monoclonal antibody, a rare earth metal, an isotope, or an autologous mitochondria;

validating the labeled biological sample by detecting a presence of the one or more first additives and comparing the detected one or more first additives to a listing of additives provided in first identifying data corresponding to the labeled biological sample;

generating an initial block of a sample tracking chain using a sample tracking engine, wherein the initial block comprises the first identifying data;

storing the initial block as part of the sample tracking chain in a sample database, wherein the sample tracking chain is indexed and thereby searchable for the first identifying data and the one or more first additives;

for each manufacturing step of a manufacturing process for generating a labeled therapeutic:

accessing the sample tracking chain from the sample database;

retrieving a previous sample state object from the sample tracking chain;

generating a current state of the labeled therapeutic, wherein the current state includes manufacturing data unique to a corresponding manufacturing step for generating the labeled therapeutic;

instantiating a current sample state object in memory as a function of the current state and the previous sample state object;

linking the current sample state object to the previous sample state object in the sample tracking chain; and updating the sample tracking chain in the sample database with the current sample state object; and subsequent to completion of all manufacturing steps of the manufacturing process, sending the labeled therapeutic comprising one or more second additives to a point of care for administration to a patient; and performing an assay on the labeled therapeutic at the point of care, thereby validating the labeled therapeutic for administration to the patient, by detecting the presence of the one or more second additives via an assay which uniquely labels the therapeutic among a population of therapeutics, wherein the validation is added to the sample tracking chain, wherein the validation includes validating a timestamp of a state block of a distributed digital ledger associated with second identifying digital data, based on an external public ledger, to confirm the state block associated with the second identifying digital data has not been modified or tampered with, and the sample tracking chain is indexed and thereby searchable for the second identifying digital data and the one or more second additives.

2. The method of claim 1, wherein the sample tracking chain comprises extrinsic and intrinsic patient data.

3. The method of claim 1, wherein the sample tracking chain comprises a linked chain of sample state objects.

4. The method of claim 1, wherein the previous sample state object comprises a previous state hash digest.

5. The method of claim 1, wherein the current sample state object comprises a hash digest generated based on the current state and a previous state hash digest.

6. The method of claim 1, wherein a different additive is added at each step of the manufacturing process.

7. The method of claim 1, wherein a different additive is added to each step of a subset of steps of the manufacturing process.

8. The method of claim 1, wherein a notification is sent to a user when the labeled biological sample fails validation.

9. The method of claim 1, wherein the one or more first additives include at least one of antigens or dyes.

10. The method of claim 1, wherein the presence of one or more first additives are detected using mass spectrometry.

11. A system for tracking a labeled biological sample through a manufacturing process, the system comprising at least one processor configured to:

receive the labeled biological sample at a manufacturing facility, wherein the biological sample is labeled with one or more first additives by inserting the one or more first additives into a container comprising the biological sample, wherein the one or more first additives uniquely label the biological sample among a population of biological samples, and wherein the one or more first additives include at least one of a primer, a monoclonal antibody, a rare earth metal, an isotope, or an autologous mitochondria;

validate the labeled biological sample by detecting a presence of the one or more first additives and comparing the detected one or more first additives to a listing of additives provided in first identifying data corresponding to the labeled biological sample;

generate an initial block of a sample tracking chain using a sample tracking engine, wherein the initial block comprises the first identifying data;

store the initial block as part of the sample tracking chain in a sample database, wherein the sample tracking chain is indexed and thereby searchable for the first identifying data and the one or more first additives;

for each manufacturing step of a manufacturing process for generating a labeled therapeutic:

access the sample tracking chain from the sample database;

retrieve a previous sample state object from the sample tracking chain;

generate a current state of the labeled therapeutic, wherein the current state includes manufacturing data unique to a corresponding manufacturing step for generating the labeled therapeutic;

instantiate a current sample state object in memory as a function of the current state and the previous sample state object;

link the current sample state object to the previous sample state object in the sample tracking chain; and update the sample tracking chain in the sample database with the current sample state object;

subsequent to completion of all manufacturing steps of the manufacturing process, send the labeled therapeutic comprising one or more second additives to a point of care for administration to a patient; and performing an assay on the labeled therapeutic at the point of care, thereby validating the labeled therapeutic for administration to the patient, by detecting the presence of the one or more second additives via an assay which uniquely labels the therapeutic among a population of therapeutics, wherein the validation is added to the sample tracking chain, wherein the validation includes validating a timestamp of a state block of a distributed digital ledger associated with second identifying digital data, based on an external public ledger, to confirm the state block associated with the second identifying digital data has not been modified or tampered with, and the sample tracking chain is indexed and thereby searchable for the second identifying digital data and the one or more second additives.

12. The system of claim 11, wherein the sample tracking chain comprises extrinsic and intrinsic patient data.

13. The system of claim 11, wherein the sample tracking chain comprises a linked chain of sample state objects.

14. The system of claim 11, wherein the previous sample state object comprises a previous state hash digest.

15. The system of claim 11, wherein the current sample state object comprises a hash digest generated based on the current state and a previous state hash digest.

16. The system of claim 11, wherein a different additive is added at each step of the manufacturing process.

17. The system of claim 11, wherein a different additive is added to each step of a subset of steps of the manufacturing process.

18. The system of claim 11, wherein a notification is sent to a user when the labeled biological sample fails validation.

19. The system of claim 11, wherein the one or more first additives include at least one of antigens or dyes.

20. The system of claim 11, wherein the presence of one or more first additives are detected using mass spectrometry.

* * * * *